(12) United States Patent
Nusimow et al.

(10) Patent No.: US 11,416,901 B2
(45) Date of Patent: Aug. 16, 2022

(54) DYNAMIC FORMS

(71) Applicant: drchrono Inc., Sunnyvale, CA (US)

(72) Inventors: Michael Nusimow, Mountain View, CA (US); Daniel E. Kivatinos, Mountain View, CA (US)

(73) Assignee: DRCHRONO INC., Sunnyvale, CA (US)

( * ) Notice: Subject to any disclaimer, the term of this patent is extended or adjusted under 35 U.S.C. 154(b) by 107 days.

(21) Appl. No.: 16/706,549

(22) Filed: Dec. 6, 2019

(65) Prior Publication Data
US 2020/0111554 A1 Apr. 9, 2020

Related U.S. Application Data

(63) Continuation of application No. 13/552,740, filed on Jul. 19, 2012, now Pat. No. 10,573,408.
(Continued)

(51) Int. Cl.
*G06Q 30/04* (2012.01)
*G16H 10/60* (2018.01)
(Continued)

(52) U.S. Cl.
CPC .............. *G06Q 30/04* (2013.01); *G16H 10/60* (2018.01); *G16H 15/00* (2018.01); *G16H 40/20* (2018.01);
(Continued)

(58) Field of Classification Search
CPC ........ G06Q 30/04; G16H 40/67; G16H 40/20; G16H 40/63; G16H 70/20; G16H 15/00; G16H 10/60; G16H 40/40
See application file for complete search history.

(56) References Cited

U.S. PATENT DOCUMENTS 5,903,873 A 5/1999 Peterson et al.
6,047,259 A 4/2000 Scott et al.
(Continued)

FOREIGN PATENT DOCUMENTS

WO 2011/084470 A1 7/2011

OTHER PUBLICATIONS

Final Office Action in U.S. Appl. No. 13/552,740, dated Nov. 19, 2018.
(Continued)

*Primary Examiner* — Eliza A Lam
(74) *Attorney, Agent, or Firm* — James J. DeCarlo; Greenberg Traurig, LLP

(57) ABSTRACT

A computer-implemented method and apparatus for development and use of a medical form. One example system receives a request on a first computer to create the medical form. The medical form includes user selected fields corresponding to patient information. The system further receives signals on the first computer, where the signals describe form fields for the medical form. The system communicates the medical form from the first computer to the first tablet device for display on the first tablet device. The system receives form values, wherein at least some of the form values correspond to information about an appointment. Responsive to receiving a completion signal, the system generates a clinical narrative for the appointment using the completed form values.

10 Claims, 22 Drawing Sheets

Related U.S. Application Data

(60) Provisional application No. 61/557,130, filed on Nov. 8, 2011, provisional application No. 61/523,223, filed on Aug. 12, 2011.

(51) Int. Cl.
*G16H 15/00* (2018.01)
*G16H 40/20* (2018.01)
*G16H 70/20* (2018.01)
*G16H 40/63* (2018.01)
*G16H 40/67* (2018.01)
*G16H 40/40* (2018.01)

(52) U.S. Cl.
CPC .............. *G16H 40/63* (2018.01); *G16H 40/67* (2018.01); *G16H 70/20* (2018.01); *G16H 40/40* (2018.01)

(56) References Cited

U.S. PATENT DOCUMENTS

| | | | |
|---|---|---|---|
| 6,941,271 | B1 | 9/2005 | Soong |
| 8,581,877 | B2* | 11/2013 | Yoo .................... G06F 3/04883 345/174 |
| 2002/0029157 | A1 | 3/2002 | Marchosky |
| 2006/0111941 | A1 | 5/2006 | Blom |
| 2007/0192137 | A1 | 8/2007 | Ombrellaro |
| 2008/0281629 | A1 | 11/2008 | Scott et al. |
| 2009/0144088 | A1 | 6/2009 | Zubiller et al. |
| 2009/0248444 | A1* | 10/2009 | Harnick ................. G16H 10/20 705/3 |
| 2009/0307755 | A1 | 12/2009 | Dvorak et al. |
| 2010/0138239 | A1 | 6/2010 | Reicher et al. |
| 2011/0166884 | A1* | 7/2011 | Lesselroth ............. G06Q 10/06 705/3 |
| 2012/0035959 | A1 | 2/2012 | Berdia |

OTHER PUBLICATIONS

Office Action in U.S. Appl. No. 13/552,740, dated Mar. 27, 2018.
Office Action in U.S. Appl. No. 13/552,740, dated Mar. 29, 2016.
Office Action in U.S. Appl. No. 13/552,740, dated Jan. 13, 2017.
Office Action in U.S. Appl. No. 13/552,740, dated Jan. 30, 2014.
Office Action in U.S. Appl. No. 13/552,740, dated Aug. 4, 2014.
Office Action in U.S. Appl. No. 13/552,740, dated Jun. 17, 2015.
Office Action in U.S. Appl. No. 14/855,725, dated Sep. 5, 2018.
Shulman, "Keeping the Record Straight," Oct. 22, 2007, U.S. News & World Report, vol. 143, Issue 14, pp. 62-63.

* cited by examiner

FIG. 9

Patient Data Menu 605
Forms Section 610
Dr. Appointment Information 620
Clinical Narrative 930
Dr. Actions Menu 660

Clinical Narrative 1020

Patient History Additional Icons 1040

Dr. Screens 700

Audit Log 1010

Record Change Review 1030

DYNAMIC FORMS

RELATED CASES

This is a continuation of U.S. patent application Ser. No. 13/552,740 (published as US20130041677), filed Jul. 19, 2012, which claims priority from U.S. Provisional Application No. 61/523,223, filed Aug. 12, 2011 and U.S. Provisional Application No. 61/577,130, filed Nov. 8, 2011, all of which are incorporated by reference herein.

FIELD

This disclosure is generally related to electronic health record systems.

BACKGROUND

Current electronic records systems for medical practices typically consist of large software systems networked together for very large medical practices. Examples of these types of systems are available from AllScripts, EPIC, and Cerner.

These systems tend to be large, expensive, fully integrated with the medical practice's information team, and inflexible. The systems do not work well for small medical groups, or allow for a high degree of flexibility in customization. Additionally the federal government is requiring medical practices to move to electronic health records in the coming years. This leaves many small medical practices without a solution to their electronic healthcare records system that is inexpensive, flexible and scalable.

BRIEF DESCRIPTION OF THE FIGURES

FIG. 9 shows an example clinical narrative for a patient appointment.

FIG. 10 shows a number of screens for reviewing patient records.

FIG. 21 shows the extended meaningful use report.

FIG. 22 shows the extended meaningful use report.

DETAILED DESCRIPTION

Overview

Figure 1:
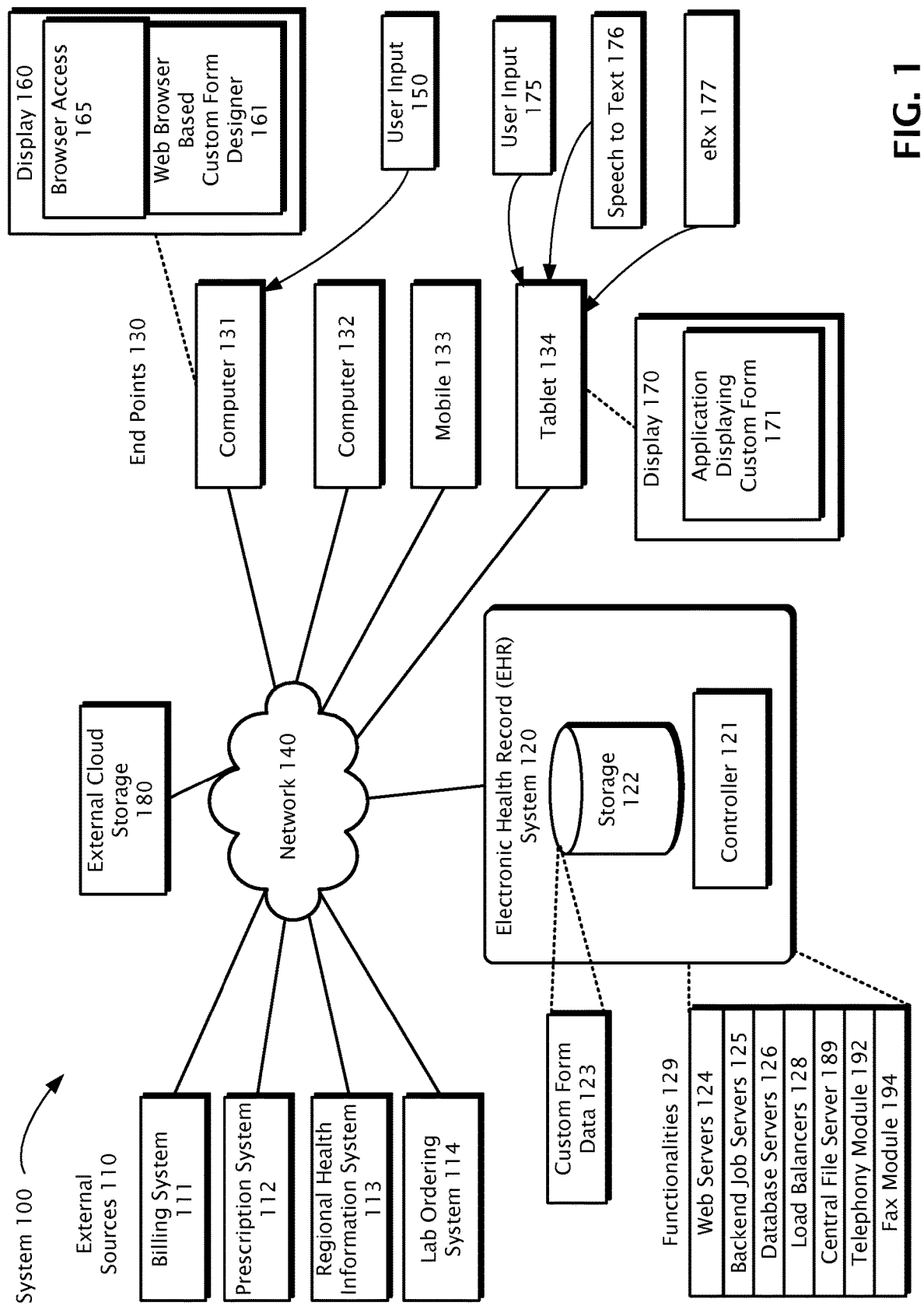
FIG. 1 shows an architectural level schematic of a system in accordance with an embodiment.

The discussion is organized as follows. First, an introduction describing some of the problems addressed by various embodiments will be presented, followed by an explanation of terminology that will be used throughout the discussion. Then, a high level description of one embodiment will be discussed at an architectural level along with a data model. Next, the user interface used by some embodiments will be discussed in conjunction with the details of algorithms used by some embodiments. Lastly, various alternative embodiments are discussed.

Consider a medical practice with a single doctor, or more generically health care provider, and optionally, one or more staff members. The doctor has patients. For reasons of efficiency as well as to comply with government mandates, the doctor may be using or considering use of an electronic health record system (EHR). For example, in the United States there is a requirement for many doctors to demonstrate "meaningful use" of an EHR for calendar years 2015 forward or they will face reduced Medicare reimbursements. Large hospital groups may be able to afford large, legacy EHR systems with a significant IT infrastructure requirement. However, smaller medical practices may find such systems cumbersome and expensive to install. A cloud-based, or software-as-a-service (SaaS), EHR offering would enable doctors to cost-effectively meet the meaningful use requirements while also improving their practices. Further, such a cloud-based system can provide social, or collaborative, features to allow disparate doctors to share information such as custom designed forms, treatment notes, and referrals, more easily.

We describe a system and various embodiments of an EHR offering that provides cloud-based, or SaaS, storage and infrastructure as well as easy use of mobile and tablet devices by doctors, staff and patients to provide an improved medical practice.

Terminology

Throughout this specification the following terms will be used:

Appointment: The term appointment refers to a patient visit, phone call, or other patient/practitioner interaction that could result in a modification of that patient's medical record. Examples include in-office appointments, phone calls, allergy shots, lab work. In some, cases an appointment is an appointment at a doctor's office where an exam room has been allocated for that patient. Importantly, appointment can used to refer to a patient appointment, to a data structure representing that appointment, and/or to a graphical representation of that appointment (e.g., on a calendar). This is also the case for other terms such as billing code, billing rule, clinical narrative, doctor, medical form, workflow, office, practice group, and other terms.

Billing Codes: The term billing codes refers to insurance codes, or other codes, that a practitioner or medical practice group may use to bill for a procedure or group of procedures. Examples of billing codes can include ICD-9-CM, CPT, HCPCS, and ICD-10 codes. The billing codes may be associated with one or more form fields to assist in billing.

Billing Rules: The term billing rules defines the set of requirements for billing for all or a part of a particular procedure. Billing rules can include requirements for patient demographics information, particular questions to be asked (and the corresponding fields to be completed). One or more billing rules may be combined to create a billing rule. Billing rules can be associated with a billing code, such that when the rule is satisfied, a billing activity may be started that billing code. One billing rule might be that if an field, form, or workflow, includes value X then generate billing code Y.

Clinical Narrative: The term clinical narrative refers to a record of an appointment. In some systems, the record can include data stored in form fields. The clinical narrative may include prescription information, answers to questions asked by the doctor, the doctor's staff, and/or the patient's own comments.

Doctor: The term doctor is used to refer generically to any health care provider, e.g. nurses, medical assistants, midwives, chiropractors, dentists, orthodontists, as well as doctors.

Form Fields: The term form fields refers to data fields in a form. Some fields may be user customizable while others may be set by the system. Some fields may be user selectable. Form fields may have location information indicating where on a display the field should be shown (or where the field should be shown relative to other elements of the form).

Locking: The term locking refers to preventing editing of one or more fields, forms, and/or clinical narrative. The data is locked until a user or someone authorized initiates an action to cause the data to be unlocked. Locking can be useful for auditing records. Then information about locking is kept, this information helps the system determine who caused what changes in the data and when.

Medical Form: The medical form refers to an electronic representation of a form, including elements of a paper medical form. A group of related data fields can be used in a medical practice group as part a clinical workflow. A number of medical forms can be completed during an appointment to form a clinical narrative. A form can be a medical form or it can be a more general version of a form.

Staff: The term staff refers to individuals working at the behest of doctors, or a practice group, to assist in patient related tasks, e.g. check in, billing, appointment scheduling, transfer of patient records and/or reports.

Onboarding: The term onboarding refers to the process of gathering information from a patient for an appointment. For example, when the patient checks in, the patient may complete a form that updates the patient's medical history since the last appointment.

Practice Group: The term practice group refers to a collection of one or more doctors potentially sharing a legal relationship. Embodiments are flexible to support various practice group arrangements. Some common arrangements include multiple doctors, shared staff, and shared patients, e.g. a patent of Dr. X is a patient of Dr. Y and both staff and doctors can see all of the records. In another embodiment, multiple doctors, shared staff, split patients is supported, e.g. a patient of Dr. X is not a patient of Dr. Y, though practice group staff can support and see EHR records for all patients. Other embodiments can handle other common situations. A medical practice group means the same thing as a practice group.

Practitioner: The term can include a doctor or a staff member or other member of a practice group. Generally, a practitioner is someone responsible for creating, accessing, and/or editing medical records and is not the patient.

Office: The term office refers to a, generally physical, location where one or more patients can be seen for appointments. In some embodiments, electronic visits are supported and in such embodiments, a virtual office location may be established.

Tablet Device: The term tablet device refers to a mobile computing device. The device has memory, a processor, a display and input capabilities. In some embodiments, the tablet device may have wireless communications capabilities. The input capabilities may include touch screen, audio, and/or video input. Examples include the iPad, Android based tablet computers, Windows based tablet computers, and tablet computers from Research In Motion, Inc. Tablet and tablet computer is used herein to mean the same as a tablet computer. In some embodiments, where a smaller screen is useful, a smart mobile phone can be used (e.g., an iPhone). What is important is that the touch device has enough computing power to process the information being received, provide a simple interactive interface (e.g., touch and/or voice), and is easily carried.

User Selected Field: The term user selected field refers to a data field that can be inserted into a medical form by a user. The combination of user selected fields creates medical forms. The user selected fields allow for the system to be flexible and customizable for each medical practice group. Users may be able to select the location of a form field for display on a form.

Workflow: The term workflow refers to a combination of forms or fields that represent some unit of work. Examples include onboarding a patient, H&P History and Physical interview and notes, and subjective objective assessment and plan (SOAP) method of documenting health care providers' notes.

System Overview

A system and processes to provide an EHR offering with cloud-based, or SaaS, storage and infrastructure as well as easy use of mobile and tablet devices by doctors, staff and patients to provide an improved medical practice is described. The system will be described with reference to FIG. 1 showing an architectural level schematic of a system in accordance with an embodiment. Because FIG. 1 is an architectural diagram, certain details are intentionally omitted to improve the clarity of the description. The discussion of FIG. 1 will be organized as follows. First, the elements of the figure will be described, followed by their interconnections. Then, the use of the elements in the system will be described in greater detail.

FIG. 1 includes a system 100. The system includes external sources 110, EHR system 120, end points 130, network 140, and external cloud storage 180. The external sources 110 include billing system 111, a prescription system 112, a regional health information exchange system 113, and a lab ordering system 114. The EHR system 120 includes a controller 121 and storage 122. The EHR system 120 provides the functionalities 129 including: web servers 124, backend job servers 125, database servers 126, and load balancers 128, a central file server 189, a telephony module 192, and a fax module 194. In some embodiments, the controller 121 provides all of the functionalities 129. The storage 122 includes custom form data 123. The end points 130 include computer 131, computer 132, mobile 133, and tablet 134. Computer 131 is coupled in communication with a display 160 showing a user interface generated within a web browser, e.g. browser access 165 and web browser based custom form designer 161. Additionally, user input 150 to the computer 131 is shown. Similarly, tablet 134 is coupled in communication with display 170 showing a user interface of an application, e.g. an application displaying custom form 171. The tablet 134 can include a speech to text module 176 and an electronic prescription module (ERx 177).

The interconnection of the elements of system 100 will now be described. The external sources 110 are coupled in communication to the EHR system 120 via the network 140. Information from the different sources may arrive via different mechanisms or all the same mechanism. For example, the billing system 111 may be retrieved over a network, e.g. the internet, private network, VPN, or MPLS circuit, using one or more protocols, such as FTP (with encryption), HTTP, HTTPS, or the like. Billing system 111 can communicate with the system 120 via the HIPAA x12 standard. The prescription system 112 may be accessed over another network, or the same network, and may be any appropriate communication protocol or an API over HTTP, e.g. SOAP, XML RPC, REST. The prescription system 112 may support ordering prescriptions for patients electronically. Other external sources (generally not shown) may include speech-to-text systems, notification systems (e.g. fax (shown internally as fax module 194), SMS (shown internally as telephony module 192), phone (shown internally as telephony module 192), email), and the like. Also, whether a given system or service is external from the EHR system 120 is an implementation specific determination. For example, if native notifications become easier to provide on the backend job servers 125 as opposed to a dedicated $3^{rd}$ party notification system, the implementation can be suitably altered.

Controller 121 and storage 122 can include one or more computers and computer systems coupled in communication with one another. They can also be one or more virtual computing and/or storage resources. For example, controller 121 may be an Amazon EC2 instance and the storage 122 an Amazon S3 storage. Other computing-as-service platforms such as Force.com from Salesforce, Rackspace, or Heroku could be used rather than implementing the EHR system 120 on direct physical computers owned and controlled by the owner of the system 100 or traditional virtual machines.

Communications between the potentially geographically distributed computing and storage resources comprising the message management system 120 are not shown. The functionalities 129 that are provided describe functional capabilities according to one embodiment and can all be provided by the controller 121 or managed by the controller 121, but implemented on one or more computing resources. For example, requests over the network 140 from end points 130 are handled in one embodiment first by load balancers 128 that distribute the requests across one or more web servers 124. The web servers can implement support for an API, e.g. RESTful, for a variety of different end points 130. The database servers 126 can manage the storage of patient information in the storage 122. In one embodiment, the database servers 126 are a mixture of traditional SQL databases, e.g. MySQL, as well as one or more media servers for storing images and videos. Additionally, the backend job servers 125 can perform periodic and repetitive tasks, e.g. submitting billing externally for patients to the billing system 111, checking the status of submitted bills, generating notifications for appointments to patients. In one embodiment, the EHR system 120 is implemented on one or more computing resources with the Linux operating system, e.g. Ubuntu distribution, with a variety of typical services, e.g. Apache web server, MySQL databases. Individual computing resources can be specialized according to the functionalities 129 provided, e.g. non-web servers might omit the Apache web server, etc. The core system can be implemented in one embodiment using Python and the Django web framework which also provides an object-relationship mapping between the data structures of the EHR system 120 and a traditional SQL database such as MySQL.

The functionalities 129 can also include a central file server 189, a telephony module 192 and a fax module 194. The central file server 189 can respond to request for specific records, for example rather than storing large images and videos directly in a database as a BLOB, a reference to the item, e.g. on the central file server 189 or on an external cloud storage 180 can be stored. The central file server 189 can respond to requests for retrieval of the item and deliver it to the end point 130. Importantly, in some embodiments, each medical record request is authenticated and the record is encrypted before transmission to the end point 130. This helps keep the medical record information secure.

The fax module 194 can support transmission and receipt of facsimiles. Doctors' offices continue to rely on facsimiles and the fax module 194 supports this practice need. A doctor can initiate a fax transmission from an end point, e.g. computer 131 or tablet 134. In some embodiments, the system 120 automatically generates a coversheet for the sending doctor. The coversheets can be a template created by that doctor, or be a preset template. The fax module 194 can support optical character recognition (OCR) capabilities to allow incoming faxes to be text searchable. The fax module 194 can allow the faxes, portion of the faxes, or the OCR'd text to be included as notes in the EHR SYSTEM 120 for a particular patient.

The telephony module 192 supports automated texting and calling (e.g., Twilio supplies such a system). The EHR system 120 can use information about upcoming appointment (see appointments 250 in FIG. 2) to automatically contact patients about upcoming appointments.

The EHR system 120 can also communicate with regional health authorities through their systems, e.g., the regional health information exchange system 113. The system 120 can use HL7, HL7.x (or other formats, e.g., XML) for communications. The types of information can include continuity of care documents, continuity of care records for patients, and/or a complete transfer of all the health data for a patient e.g. all the medical history the doctor has for a patient.

The system 120 can also communicate with a lab ordering system 114 to allow a doctor to request a lab order, or receive lab results. Examples of companies that support such a system include Quest and Labcorp. The system 120 can communicate via HL7 messaging to allow the doctor to enter a lab order and receive data in e.g., HL7, XML format and/or in HTML format.

The EHR system 120 can also include, or communicate with, external cloud storage 180—e.g., Dropbox. This may be used to store some documents in an alternative cloud location as a backup, or as another access point for data. The system 120 allows the doctor to select which material to store and how. For example, some data could be unencrypted, e.g., patient education material or doctor education material. Encrypted data could include health information such as x-rays, MRI's, videos, and other patient and clinical information. The external cloud storage 180 may facilitate data sharing over the world wide web without access to the EHR system 120. In one embodiment, the EHR system 120 writes encrypted files to the external cloud storage 180 and a doctor can access those files from any computer using the decryption keys.

The speech to text program 176 can convert audio received on the tablet 134 to text. Such a system is available from M*modal Technologies for example. In one embodiment, the EHR system 120, in conjunction with an application on the tablet 134 and the speech to text program 176, tracks corrections to the speech to text. This can be helpful in providing feedback to the vendor, or generally tracking errors. In some embodiments, the application 171 shows when to start speaking, when to stop speaking, and/or when there is too much background noise (or other poor audio quality issues). The application 171 can provide this with visual cues (e.g., red light/green light)

The tablet 134 can include an electronic prescription application, e.g., ERx 177 available, for example, from Remedy Systems Inc.

The end points 130 are similarly coupled in communication to the EHR system 120 via network 140. This communication is generally over a network such as the internet, inclusive of the mobile internet via protocols such as EDGE, 3G, LTE, WiFi, and WiMax. The end points 130 may communicate with the message management system 120 using HTTP/HTTPS protocols and may be implemented in one embodiment using a web interface or application to enable easy support of a range of end point device types. The mobile 133 can be any mobile device with suitable data capabilities and a user interface, e.g. iPhone, Android phone, Windows phone, Blackberry. The tablet 134 can be any tablet computing device, e.g. iPad, iPod Touch, Android tablet, and Blackberry tablet. According to some embodiments, the end points 130 are any web-enabled device supporting reasonably full HTML rendering, and the feature set available on a device may be limited depending on the HTML rendering capabilities. In other embodiments, a custom, or native, user interface is prepared for the device, e.g. a device with a more limited web browser but a native widget set might receive a custom application. Similarly, some recent mobile devices and tablet devices support an "application store" concept and custom applications could be targeted at such embodiments. In certain situations, the environment may be executing remotely and rendered on the device, e.g. cable headed computers execute the application and cause the display to be rendered and process user inputs passed back over the system (not shown). The display 160 is coupled in communication with the computer 131 and the computer 131 is capable of receiving user input 150, e.g. via keyboard, mouse, track-pad, touch gestures (optionally on display 160). The display 170 is coupled in communication with the tablet 134 and the tablet 134 is capable of receiving user input 175, e.g. via touch gestures on display 170, a camera on the tablet 134 (not shown), or other sources.

Figure 2:
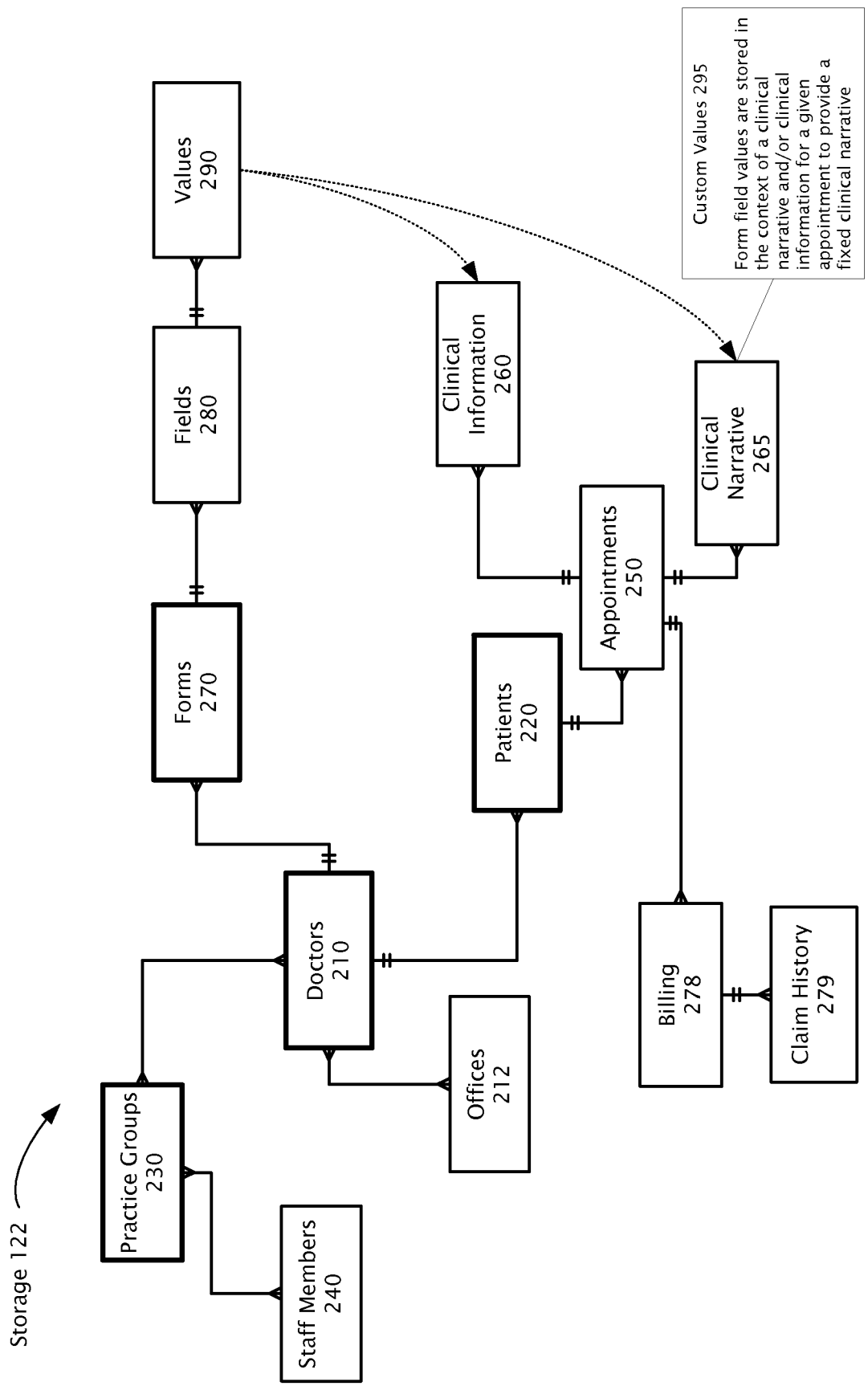
FIG. 2 shows a high level view of the data model of a system in accordance with an embodiment.

Having described the elements of FIG. 1 and their interconnections, the system will be described in greater detail in conjunction with FIG. 2, showing a high level view of the data model of a system in accordance with an embodiment.

FIG. 2 shows an example relationship between data representing doctors 210, patients 220, practice groups 230, and forms 270 (all shown in boxes with heavier lines) as well as several ancillary relationships with staff members 240, offices 212, appointments 250, clinical information 260, clinical narratives 265, fields 280, and values 290. The lines between these boxes, together with the notations at the line ends, describe the cardinality of the relationships, e.g. each appointment 250 is related to one patient 220, while each patient 220 may have zero or more appointments 250. The singular and the plural are used interchangeably in discussing the elements of FIG. 2 for clarity to better focus on describing the data model which the diagram describes. Additionally, not shown is the storage of custom values 295 into the clinical information 260 and/or the clinical narrative 265 corresponding to custom form data 123 on FIG. 1. This storage is important because, for example, for a given appointment 250 that occurred yesterday, the form 270 used (e.g. Diabetes checklist) had specific questions, answer choices, and answers (e.g. values). The clinical narrative 265 corresponding to the use of that checklist should not change if the doctor 210 updates the Diabetes checklist form 270.

In an embodiment, the patient 220 can include a portion that can be private to that patient. The patient can then decide whether to expose all or portions of that private record to the doctor. Similarly, other embodiments provide a capability for partial entry of initial symptoms by a patient via one or more standardized forms. For example, by allowing the patient to directly type or dictate a short narrative of their symptoms into a form, which is then shown to the doctor, errors can be reduced. One particularly useful feature is to ask the patient to update their list of medications currently being taken. In one embodiment, such patient entries are not directly entered into the patient's clinical information 260 until the doctor specifically approves the entry of the information (the system 120 then locks the data). The medication list example is a good example of why the patient's data entry should not directly be entered into the medical record; the patient may have selected wrong medications (sound-a-likes, misunderstandings, picking a brand name when they take a generic, etc.). However, the fact that the patient started the data entry directly into the system can reduce errors versus having the patient dictate to a staff member who writes it down and then the doctor enters the information.

FIG. 2 is only one possible data model used by an embodiment; other data models may be used. It should be understood that the data model in FIG. 2 can be implemented in one or more databases, object relational mapping (ORM) systems, and/or any other appropriate data storage. In one embodiment, the ORM from Django is used to directly map Python data structures to one or more SQL database stores. For purposes of this discussion, in the context of an SQL-style database, each box loosely corresponds to a tablet with rows of the tables containing the appropriate contents. For example, the doctors 210 could be stored as a tablet with one row per doctor, and an intermediate tablet would be used to connect the doctor tablet with the practice groups tablet support the many-to-many relationship. In other data storage approaches, intermediate tables might not be required, and for that reason such intermediate, or join tables, are omitted from the data model of FIG. 2. The data and data model of FIG. 2 can be stored in the storage 122 and managed by the controller 121.

Discussing the data model of FIG. 2 further, the offices 212, doctors 210, patients 220, and appointments 250 data can be used for scheduling. In some embodiments, the EHR system 120 provides appointment-scheduling functionality. This may include providing a web based interface to end points 130 for use by patients in their home to directly schedule appointments. Additionally, the system can allow staff members 240 to schedule appointments 250 for patients 220 via a web interface. In some embodiments, the staff interface for scheduling provides greater functionality than the patient interface, e.g. more direct access to specific open appointment times, etc.

The forms 270, the fields 280, and the values 290, allow doctors 210 to create custom forms and store custom form data as part of the clinical information 260 and/or clinical narrative 265 of an appointment 250. For example, a Diabetes specialist might have one or more forms, checklists, or other documents that they like to use to record their patient interactions and observations. For example, one checklist might relate to capturing information about the patient's lifestyle, e.g. eating patterns, exercise levels, and the like. That information might assist in prescribing decisions, longer term retrospective correlation and discussion of lifestyle information with other test results, etc. As described later, the doctor 210 (or in some embodiments staff members 240) can directly design a form 270. The form 270 can have one or more fields 280 for capture of information, e.g. values 290. The data model shown is one model for supporting storage of the custom fields and values in a database. As discussed above, the provision of a fixed clinical narrative is important medically and legally so the custom values may also be frozen in place, replicated into other parts of the data model, and/or otherwise placed into a narrative to assist in that function.

In some embodiments, forms 270 can be grouped into workflows. In such systems, the workflows related data structures may be added as part of the data model of FIG. 2.

Some embodiments support sharing of forms 270 outside of just a single practice group 230, to any doctor 210 using the EHR system 120. In some embodiments, there is an easy way for doctors 210 to email, blog, or post to social networks a given form 270. The receiving doctor 210 can use that form 270 directly (without modification) or may modify the form 270 to better suit their needs. In some embodiments, each form is assigned a unique identifier that can be used to access that form within the system 120. This allows a doctor to post the unique identifier and allow another doctor to access the form using that unique identifier. In some embodiments, a doctor can forward a unique identifier that can only be accessed by the recipient.

Turning to the appointments 250, they can initially be created at the time of scheduling, e.g. Samantha Jones has a 10 am appointment with Dr. West at the 123 Main Street office for a routine diabetes checkup in exam room 3. The appointment 250 can trigger one or more notifications generated by the EHR system 120, e.g. controller 121. At the time of check-in, a staff member can provide the patient an end point 130 for self-check-in, e.g. tablet 134. This direct-user approach may support a number of useful features, e.g. photo capture of patient, photo capture (scan) of insurance card, direct patient entry of demographic, ethnographic, billing, and/or insurance information.

During the visit, the doctor can use one or more forms 270 (either custom or system provided) to update clinical information 260 that is associated with the visit. For example, storing a record of currently taken prescription drugs is a common set of information captured. The EHR system 120 can then automatically generate a clinical narrative 265 for the visit from the doctor entered information. Usefully, the tablet 134 allows the doctors to more directly face patients during visits as opposed to staring at a screen and keyboard on a personal computer. Similarly, the tablet interface supports direct viewing and annotation of images and video such as x-rays, CAT scans, and/or faxes. For example, for a dermatologist, a skin lesion could be photographed and then annotated on the device. Using speech-to-text, the doctor could more easily dictate a memo. The entire clinical narrative 265 for the appointment 250 (optionally including images, whether or not annotated) can be sent (e.g. secure electronic transmittal or facsimile) to another doctor even if they are not using the same EHR system 120.

The data model of FIG. 2 supports storage of billing information (e.g. billing 278), which can include the billing codes. The billing information may be automatically generated from the forms 270. The billing information can also be related to an appointment 250. The billing 278 however is only a portion of the picture, the claim history 279 includes transactional information about the EHR system 120 submission of the claim, e.g. to billing system 111, and subsequent responses. Presently, it is common for a number of claims to need to be resubmitted, e.g. with additional supporting information, recredentialing of the doctor, clarifying information about the patient, etc. The EHR system 120 includes workflow processes for handling rejected claims and tracking the history of claims via the claim history 279. Additionally, this data allows reporting about average reimbursement rates, e.g. you normally bill $1,000 for a given procedure but your average reimbursement rate is only $400.

Notably not directly shown in FIG. 2 is the storage of information about the patients 220 (e.g. insurance), or the storage of test results, images, videos, correspondence, annotations, and the like some of which may be stored within the data model directly (e.g. BLOB) or which may be stored outside the database (e.g. pointer or URL to storage of the item on a media server).

In summary, the architecture of system 100 and the components and mechanisms through which it affords an easy way to provide a an EHR offering with cloud-based, or SaaS, storage and infrastructure as well as easy use of mobile and tablet devices by doctors, staff and patients to provide an improved medical practice.

Some additional embodiments and features are described in the below:
A. Patient Onboarding Application
B. Doctor Application
C. Website Interactions Examples
D. Additional Form Creation
E. Example Templates
F. Sample Meaningful Use Report
G. Conclusion and Additional Embodiments The contents of these additional embodiments and features will now be described in detail.

A. Patient Onboarding Application

The following describes the patient onboarding application. This application may be installed on a table 134, e.g., an iPad as an app, and can be used by a practice group to update information about their patients. The application is simple enough for a patient to use while sophisticated enough to fully function in the onboarding process. In particular, the application allows a practitioner to select an appointment for a given patient, from a list of patients and appointments, and then hand the table 134 over to the patient. Onboarding a patient can involve receiving information about a patient's demographics, identification, medical history, allergies, current drugs, health care insurance and/or a description of the current problem the patient is addressing. Often onboarding can be done at the start of an appointment. For new patients, the practitioner can create a new patient record and allow the patient to input the information. For existing patients, the application can be used to update those patients' information. The following illustrates and onboarding process.

In some embodiments, separate apps exist for doctors. In other embodiments, the patient onboarding and the doctor application can be combined, and include controls for selecting whether the onboarding workflow or the doctor workflows are to be selected. FIG. 3 through FIG. 11 illustrate example embodiments where two different applications are used, one for onboarding and updating patient information, and a second application for use by the doctor.

Figure 3:
FIG. 3 shows a screen used by a practitioner for onboarding patients.

FIG. 3 illustrates the home screen of the patient application used in the onboarding process. The screen shows a list of patient's appointments 310, specific information about a particular patient and their appointment (appointment information 320), actions that can be taken on that patient's health record (patient actions 325), a notes field 330, and an actions menu 340. The appointment list 310 allows the practitioner to select the specific patient for onboarding. Appointment information 320 can display a brief summary of the selected patient appointment including demographics information and appointment information. Additionally in some embodiments, the iPad can be used take a photo of the patient. This photo can be associated with the patient's records and displayed on the screen allowing doctors and practitioners to identify the patient with the appointment. The notes field 330 allows the practitioner to enter notes about the patient's appointment. The actions menu 340 at the bottom of the screen allows the practitioner to perform other activities within the application such as to lock the screen (important for patient confidentiality), chat with other members of the practice group, and select the online help system. The patient actions menu 325 allows the practitioner to schedule additional appointments or modify the existing appointment. At the top of the screen, a new patient button is shown. Here a practitioner can create a new patient record.

In some embodiments, the notes field 330 can be one tab of a set of tabs allowing accessing to information about that patient or appointment. For example, tabs for summary info, medication list, patient demographics, and/or patient profile information, can also be accessed through tabs in the approximate location of the notes field 330. In some embodiments, the tabs may be color coded or provide a visual indication (e.g., a check mark) to show which part of a patient's profile needs to be (e.g., missing data, out of date data) and/or has been updated (e.g., the patient or staff updated a field). These indicators provide for easy checking of missing, new, or outdated information.

The settings button 350 allows users to turn on or turn off sample data across all of the screens and views within an application. This is particularly helpful when demonstrating the system 120 to prospective users or when a user is attempting to illustrate a problem or concern and does not want to expose real patient data. The sample data can be turned on by default in some embodiments. In other embodiments, the sample data is randomized actual patient records.

Note that the appointment list 310 can be a list of patient appointments for that doctor. The list can be generated from the appointments calendar for that doctor (based upon who signed in to the application). For some practice groups, the doctors can see all the patient appointments and in other practice groups, only the specific doctor's appointments are viewable by a doctor (this can be user settable).

The patient search box 360 lets the doctor find a random patient in the system 120. This can be useful for a walk-in patient.

The practitioner is able to easily set up an appointment by selecting the schedule button from the patient actions 325. In some example systems, appointments in four weeks, one month, three months, six months, or a year can be selected and the office location and the specific examination room can be selected. Once an appointment is set, an acknowledgment indicator such as a pop up can be displayed. The scheduling feature can be helpful when the patient is a walk-in, or at the end of a patient's appointment.

Figure 4:
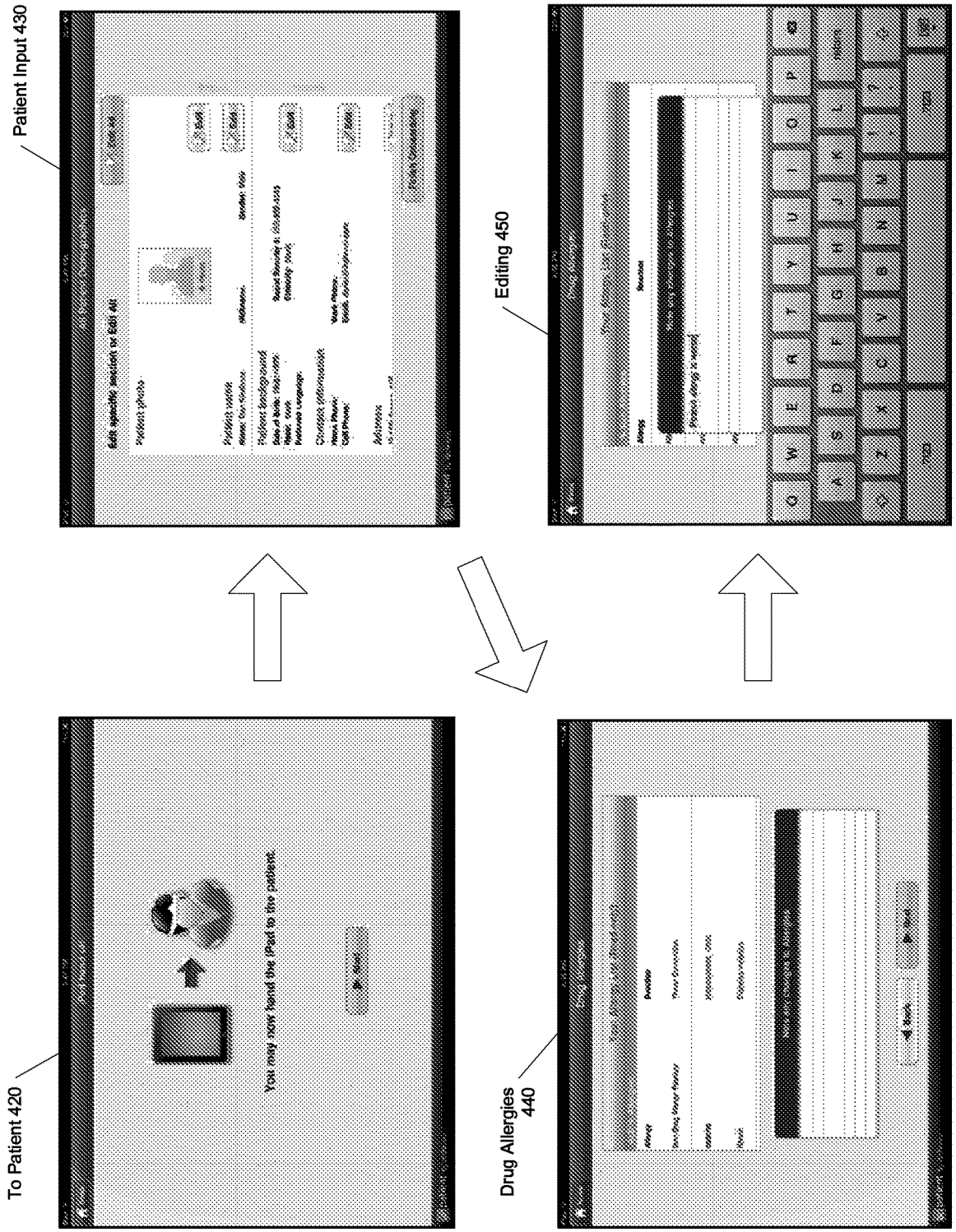
FIG. 4 shows a number of screens used by a patient to input information for an appointment.
Figure 5:
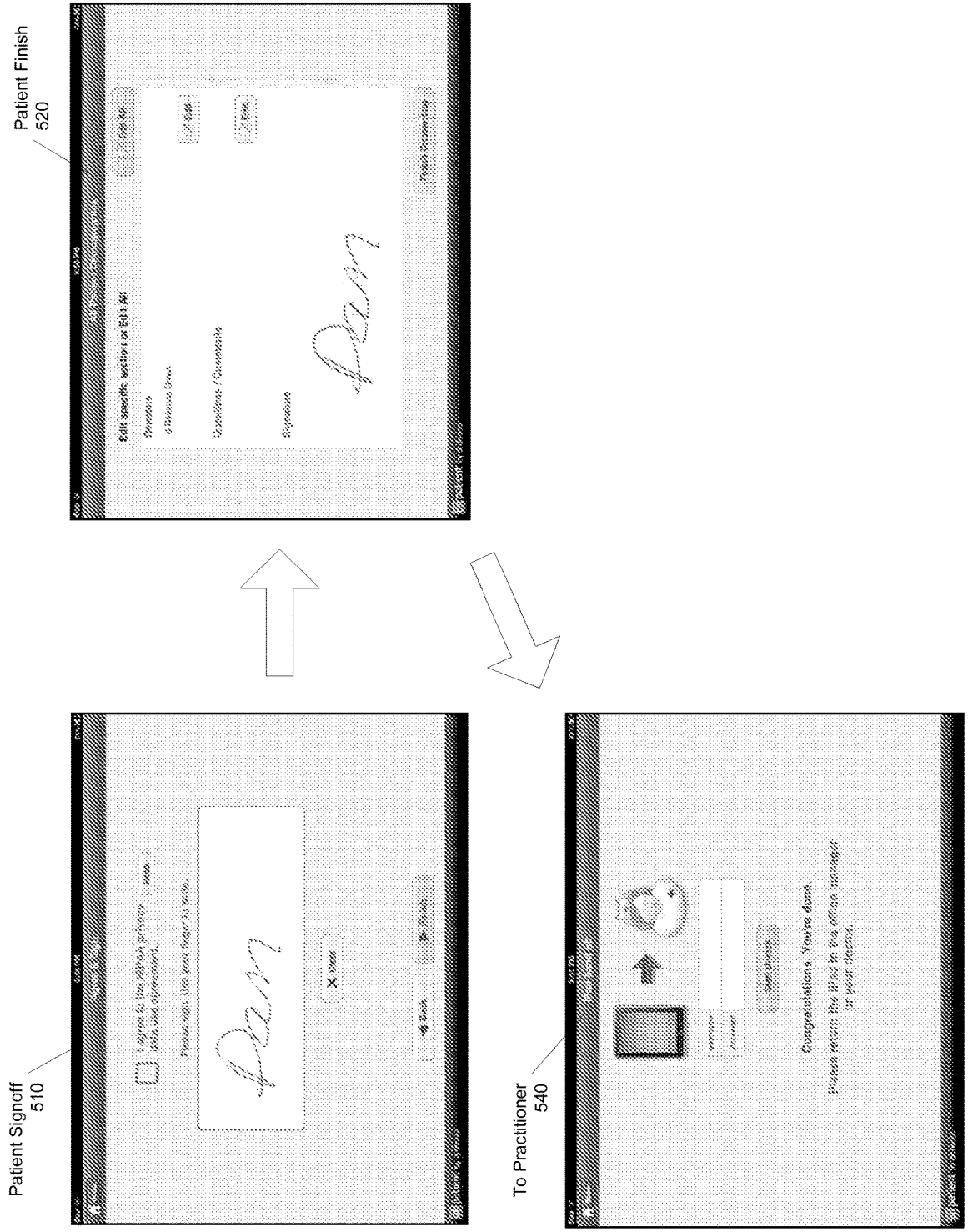
FIG. 5 shows the conclusion of the patient onboarding process and the screens for returning the tablet computer to the practitioner.

When the practitioner wants to onboard a specific patient, they select that appointment 250 from the appointment list 310 and select the start onboarding button from the patient actions 325. FIG. 4 and FIG. 5 illustrate the display for the onboarding process from this point on. The To Patient 420 screen is then shown. The to patient 420 screen signals to the practitioner to pass the tablet to the patient for further onboarding. In some embodiments, this screen shows basic identification information to the patient so that the patient can confirm that they are correct patient and therefore they will be updating the correct medical record information. In some embodiments, the icons show a graphic of a practitioner passing the tablet to a patient. In some embodiments, the person's first and last name, the last 4 digits of their social security number, their home street, and or a picture of that patient, are shown on this screen. In some embodiments, the patient can then accept or reject that they are the correct patient. These additional features help ensure that the correct patient record will be given to the correct patient for updating.

In some embodiments, the patient is allowed to select the language they wish to use to complete the patient onboarding information. For example, the to patient 420 screen may allow include buttons, text and/or other graphics allowing the patient select Spanish. The system 120 then continues with the rest of the patient onboarding using Spanish templates and forms stored in the system 120. In some embodiments, the notes, comments, and fields that the patient inputs are translated into the doctor's and/or practitioner's preferred language. This translation can be done on the end point 130 or on the EHR system 120. In some embodiments, the form fields are automatically translated, in others, the form fields are selected by a practitioner or doctor with specific knowledge of the language that the specific form will be using (for example, the doctor may make an English form and then also make a Spanish form—specifically editing field names using the form editor).

In some embodiments, when the tablet computer 134 is to be passed between the patient and staff, and/or between appointments, the display may include a graphic indicating that the tablet computer 134 should be wiped to prevent the transfer of bacteria or diseases. For example, when the patient passes the tablet computer 134 back to the staff, and the staff log on, they are reminded to disinfect the tablet computer 134. In other embodiments, the graphic reminds the doctor to wash their hands after an appointment.

Each patient's privacy is very important. In some embodiments, individual patients are not allowed to access information about other patients. Therefore while onboarding one patient is locked out of being able to access other patients' information. The screens presented to the patient do not allow the user to select other patients. Only the practitioners can select new patients for accessing their demographics information. Even if a patient exits the application, in some embodiments, the application requires a user to enter a passcode or password to return the application to the patient onboarding section.

When ready, the patient selects the start button from the to patient 420 screen. The patient input 430 screen shows that the patient is now presented with their patient demographics fields. The patient can edit all of the fields or just specific ones. The patient can review information such as their contact information, their home address, cell phone number, home phone, e-mail address, emergency contact information, employer information, race, gender, insurance information, date of birth, and/or the patient's Social Security number. The patient can also update allergy and descriptions of any current problems they are having.

Drug allergies 440 shows editing an example field—the list of the patient's allergies. In some embodiments, not all of the fields are directly editable by the patient. Here the patient is allowed to comment on the allergy information but not directly update the information. In this example, the updating of this information is restricted to the practitioners only. The reason is because if the patient accidentally changes information here, the health of the patient could be put at risk (for example, accidently deleting an allergy to a particular drug could be deadly for that patient). Editing 450 shows the application being used by the patient to add just such notes. The patient notes can be reviewed by the practitioner and then the appropriate field can be updated or further inquiries can be made. In some embodiments, the practitioner is specifically prompted to sign off or acknowledge that they have reviewed each of the patient's notes and/or changes in their medical record.

In this specific example, editing 450 shows the patient updating their information about their allergy to peanuts. As noted above, in some embodiments, only the note is saved, the patient cannot make a direct change to the allergy list. The note is then saved. The patient moves between the fields in the onboarding form to complete the onboarding process.

Patient signoff 510 shows the end of the onboarding information for a patient. The patient is asked to review and agree to the HIPAA privacy data use agreement and sign the document. Also illustrated is one of the benefits of using a touchscreen device; it is very easy for the patient to sign and interact with the touch device. Here the patient is signing that all the fields have been completed/updated. The patient signs their name with their finger or a stylus.

Patient finish 520 shows the signature of the patient as sign off by the patient that their information has been updated and is complete. When complete the patient pushes the finish onboarding button.

The To Practitioner 540 screen is then shown. This screen indicates that the patient should return the iPad to the practitioner. The patient is prevented from accessing other patient's records. The practitioner is prompted with their username and password to unlock the application. In some embodiments, the practitioner can enter a pin code, in others, pin codes may not be used because they may be too easily guessed. In some embodiments, the pin code is disabled after a specific period of time (e.g., 20 minutes, or a user programmable period, or after a specific number of failed attempts). In some embodiments, the system prevents users from using very simple passcodes (e.g., all the same number, 1234). In some embodiments, a restricted connection is used to unlock the tablet 134. The tablet 134 can include near field communications capabilities or wired connectivity, and only after the restricted connection is established, is the application unlocked.

In some embodiments, pictures of the healthcare insurance card can be captured by the device. In other embodiments, credit card information can be captured. In other embodiments, flexible spending account information can be captured and receipts generated and automatically sent to the patient's flexible spending account plan. In other embodiments, the insurance information can be used to check eligibility with the insurer immediately—e.g., the EHR system 120 would communicate with an insurer directly or through a clearinghouse for the insurers and check that the appointment will be covered.

B. Doctor Application

In some embodiments, doctors and patients use different application. The patient onboarding application is suited for providing onboarding information and may be restricted to allow for a simple interaction by the patient. However the doctors will often want to do more than simply onboard the patient. Therefore a second application may be included in different embodiments of the invention. This application can be similar to the patient application but includes more actions and more capabilities. For example, the doctors application can include the appointment list 310, appointment information 320, the ability to view a patient's chart, a notes field 330 and an actions menu (including prescription related actions or take a picture).

Figure 6:
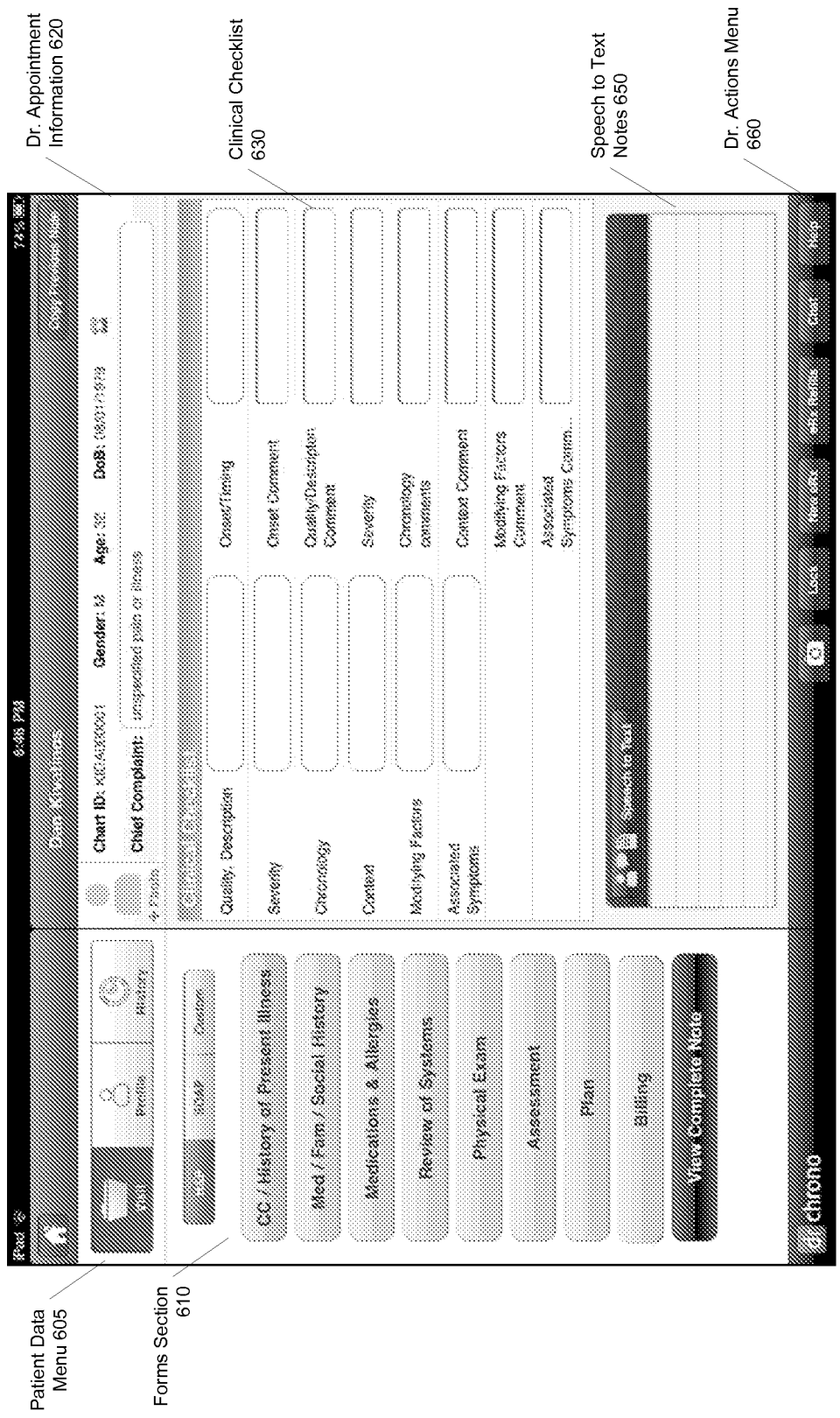
FIG. 6 shows a screen for a doctor to use during a patient encounter.

FIG. 6 shows the screen after a doctor has selected a patient ("Dan Kivatinos" in this example) and selected the patient chart button. To help the doctor with context, the Dr. appointment information 620 includes information about the specific patient such as age and ID and the cause for the appointment.

From the patient data menu 605, the doctor has selected the visit button to start the workflow for a visit. The forms section 610 shows forms that the doctor can select to fill out for the visit. These forms can be customized forms generated for the doctor's specific practice. These forms create a workflow for that doctor. The system 120 can automatically update the forms on the iPad if any changes are made to them. Forms may be grouped according to different categories which are programmable by the doctor or someone in the doctors medical group (these groupings can form a workflow). In this example, the form presented is for helping the doctor walk through a checklist associated with a history of the present illness.

The example clinical checklist 630 is shown in the middle (and can be scrollable). Importantly, the form fields in the clinical checklist can be user selectable. Not only the names and types of these fields can be selected, but in some embodiments, the relative location of the field on the display 160 can be selected. In other embodiments, the relative location of fields with respect to each other on a form can be selected. This high level of customization allows for each practice group and/or doctor to have their very own set of forms.

The speech to text notes 650 allows for typed of speech to text recording for the doctor (the doctors can speak their notes into this field and have them converted to text).

The proximity of the visit workflow to the H&P button and to the specific forms is an intentional feature to make the interface easier for the doctor to use.

Once the clinical checklist 630 is completed, the doctor can move onto the next form in the forms section 610. For example, the doctor can select the medical family and social history checklist. The doctor can then review each of the fields and provide an update to the patient's medical record. Importantly these fields can be pre-populated based on how they were programmed for that particular doctor's practice.

Figure 7:
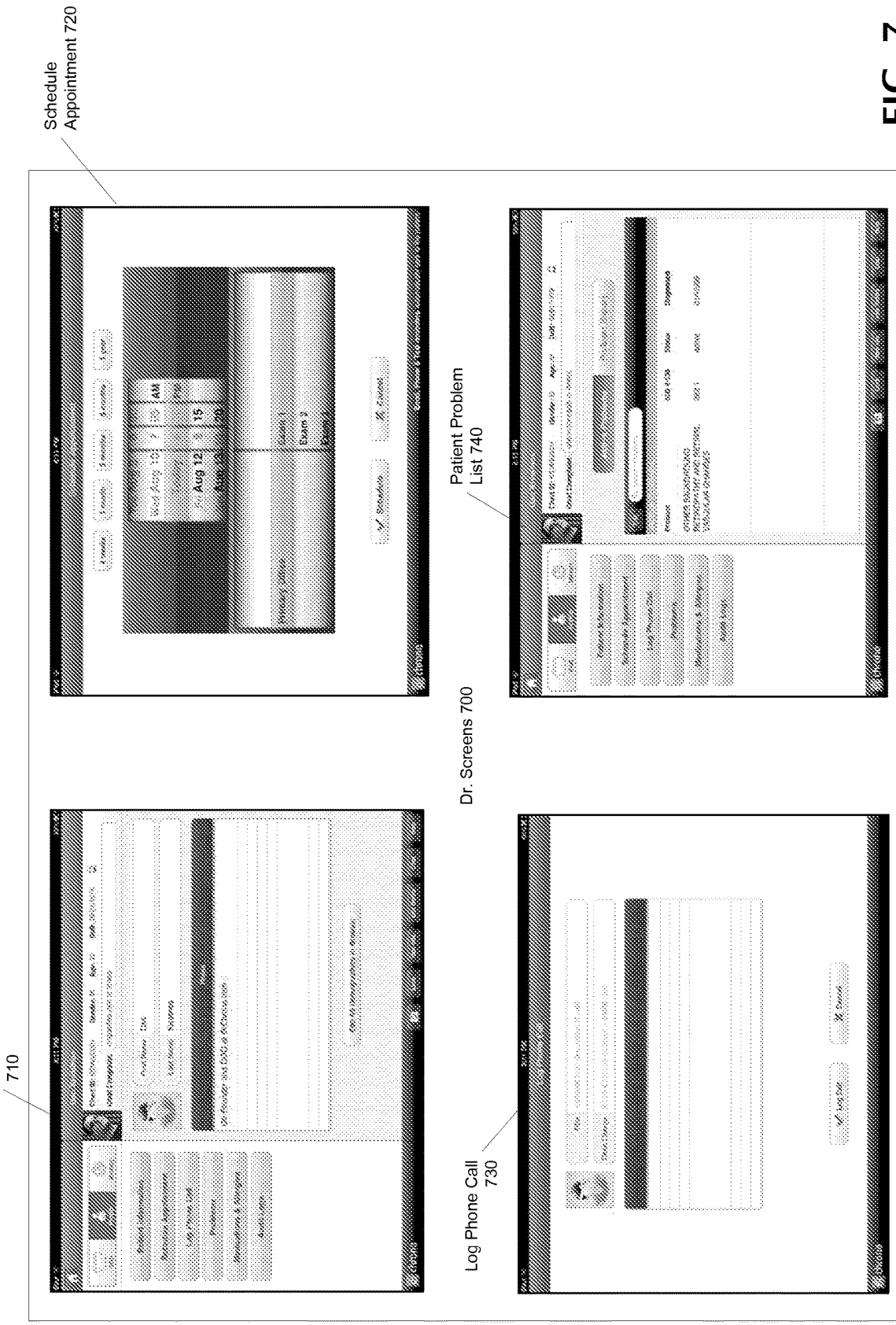
FIG. 7 shows various doctors screens allowing the doctor to input information during a patient's appointment.

FIG. 7 illustrates additional doctor screens 700. For example, here the doctor selects the patient profile button and patient specific information. Patient profile 710 includes the patient's demographics information from onboarding. The doctor can then add any additional. In some embodiments, the doctor is prevented from modifying the onboarding information in this app, in others; the doctor may only modify some parts of the onboarding information. Also, this screen can be used for walk-in patients or for phone calls. This screen allows the doctor to update the patient information outside the context of an appointment.

Schedule appointment 720 screen shows that the doctor can schedule the next appointment for the patient. Much like the scheduling capability in the onboarding application, the doctor can schedule an appointment for the patient. This is particularly helpful where the doctor has a small practice.

Log phone call 730 screen shows that the doctor has selected the log phone call button from within the profile menu selection. Here the doctor can log information from a phone call for that patient. In some embodiments, the logging of the phone call can trigger a billing code. The logged phone call can become part of the electronic health records for that patient.

Patient problem list 740 shows that the doctor has selected the problems button. The doctor can then review any active problems or any problem history that the patient has. The doctor can then select one of the problems and be provided with a complete history of that particular problem.

Figure 8:
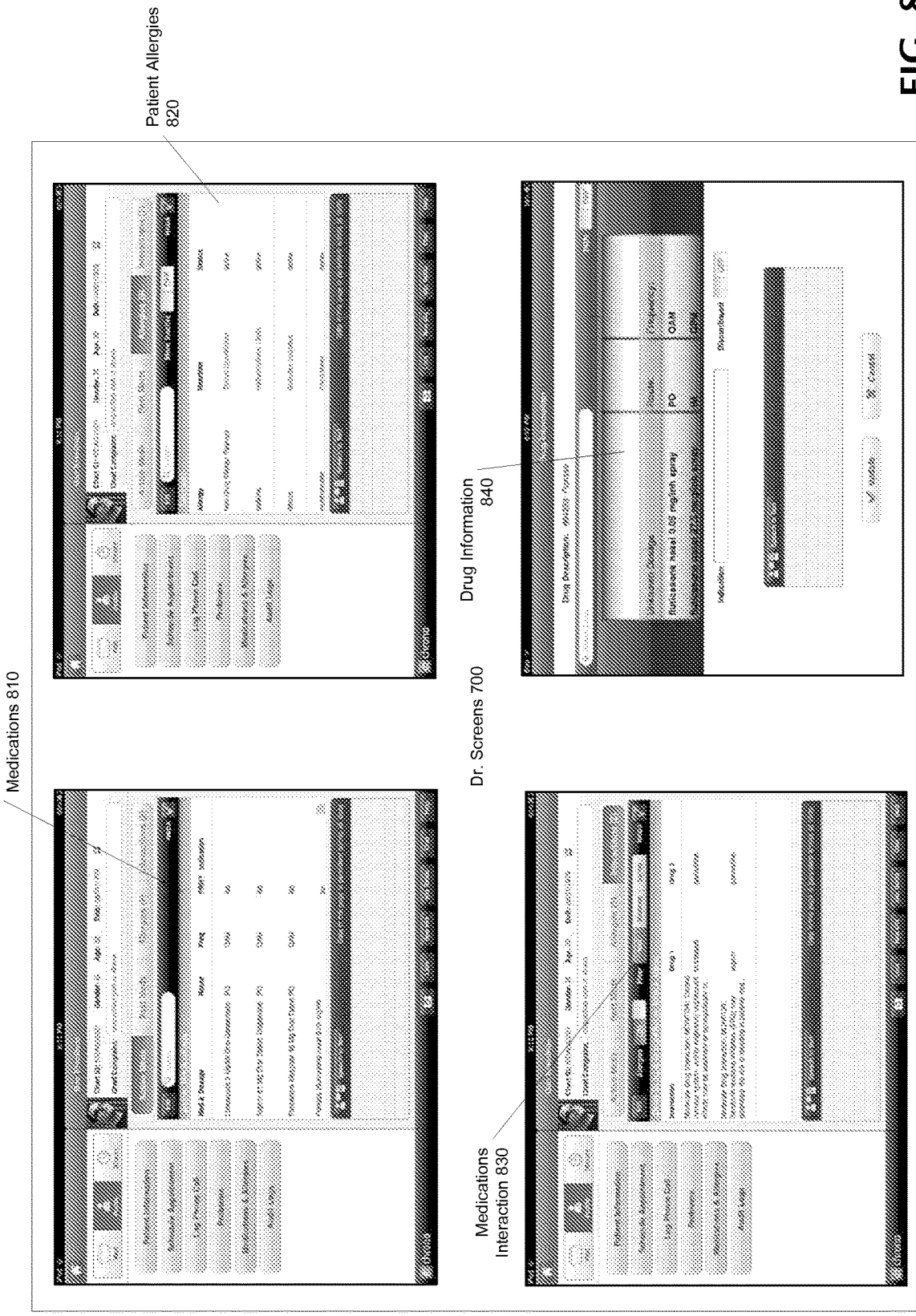
FIG. 8 shows screens for inputting information about patient medications and allergies.

FIG. 8 illustrates reviewing and ordering medications. Patient medications 810 shows what medications the patient is currently using. Returning to FIG. 1, the patient medications 810 screen can be produced on the tablet 134 on the display 170 via the application displaying the custom form 171. Note, as is the case in patient medications 810 where no custom form is displayed, the application displaying the custom form 171 does not always have to be displaying a custom form. shows the medications and allergies for the particular patient. The application 171 causes the tablet 134 to connect wirelessly through the network 140 to the EHR system 120. The controller 121 accesses the particular functionalities 129 (e.g., the database servers 126). The database servers 126 then process queries to access information for the patient out of the patients 220 data structure. The prescriptions data structures is not shown in FIG. 2, but is included in some embodiments of the invention. In other embodiments, the prescriptions information for the patient may be accessed from other services such as the prescription system 112. Patient medications 810 shows active medications as well as allergies and drug interactions. Past medications can also be reviewed. Patient allergies 820 shows drug to drug and drug allergy interactions. Medications interactions 830 shows interactions between medications and their relative severity. The doctor then can select one of these items and get more information, e.g., from prescription system 112. Specific drugs can then be investigated by the doctor as well and any current dosage recommendations—patient specific dosage information can be entered by the doctor shown in drug information 840 screen. The doctor can also search for new information on new medications for the patient. The doctor can use the speech to text field to capture additional information about the prescription such as particular concerns that the patient has about the drug.

In the doctor actions menu 660, the doctor can also prescribe or refill prescription medications. In some embodiments, the system 100 interacts with third party for prescribing drugs. In this example, the doctor selects the new prescription button and is presented with a pop-up that allows the doctor to prescribe prescription for that patient. In one embodiment, the prescription system is provided by Remedy Systems Inc. The doctor can also obtain information about other prescriptions, address refill requests, investigate prescription problems, and review any alerts or messages. In some embodiments, the EHR system 120 provides up to date patient information to the prescription system 112. Examples of this information are home address, phone number, name, age, and/or gender. In some embodiments, drugs and/or allergy information can be sent as well. In some embodiments, the EHR system 120 provides insurance information so that the prescription service can provide formulary information back to the doctor.

Figure 9:
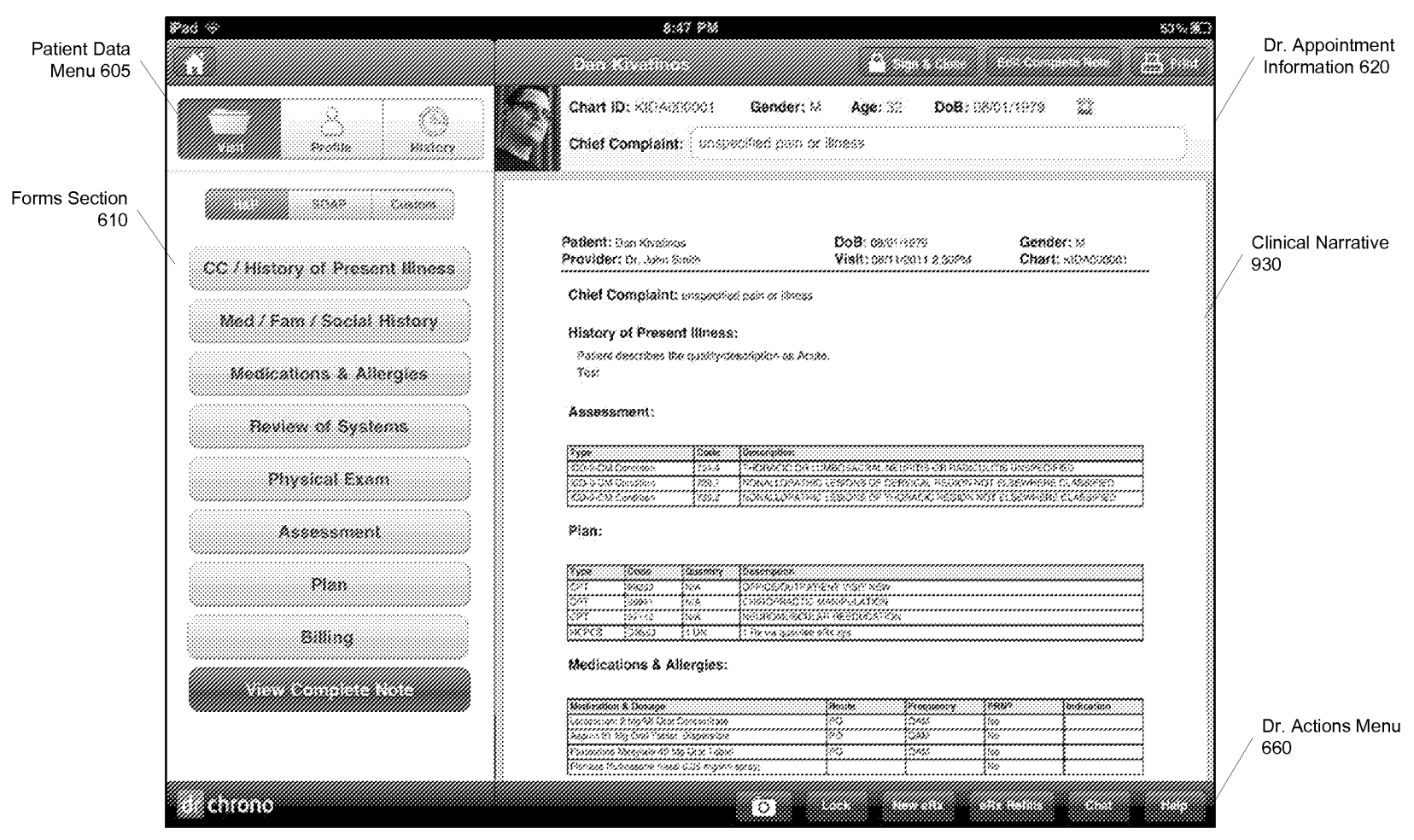

Returning to the patient appointment workflow, FIG. 9 shows that a complete clinical narrative 1020 can be generated for a patient appointment. The narrative includes any of the notes that have been entered by the doctors and any assessments, plans, medications and allergies, for example. This can represent the legal and medical record for a patient's appointment. Importantly, the clinical narrative 1020 can be generated by the EHR system 120 using the values 290 for the forms 270 and related fields 280 that have been completed for the appointment. In the example shown, the patient supplied information, staff supplied information, and doctor workflow information, are all combined into a single document. At the end of the appointment, the doctor selects the sign & close button. This allows the doctor to indicate that a doctor has signed off on a complete clinical narrative 1020 for a patient visit. The system 120 locks the record and the doctor must select the unlock button to go back and change the notes. Locking a note can start a billing process automatically. Locking and unlocking can be logged in the audit log.

FIG. 10 shows screens that are particularly helpful for electronic health records. The doctor has selected the audit logs button and can now see everyone who has opened and/or edited the records for a particular patient (shown in the audit logs section 1010). The doctor has the option of selecting whether all accesses should be shown, only those that wrote to the records, or only those that read from the records. The doctor then selects the patient history button. The clinical narrative 1020 for past appointments can be shown. Note that in this example, the clinical narrative shown is for the appointment that was just completed. In some embodiments, the patient history requires that the workflow be completed and signed off by the doctor before the clinical narrative 1020 would be displayed in the patient history. In other embodiments, the audit logs show that the records are being edited, but are not closed. We can see that there is a clinical narrative of a visit on Aug. 12, 2011.

The doctor can review each change to the medical records. For example, record change review 1030 shows the HIPAA signature that the patient entered using the onboarding application (described above).

The history can include other types of historical data for the patient (e.g., lab results, x-rays, MRI's, photos, video, and audio). This historical data can be tagged by the EHR SYSTEM 120 automatically based upon the kind of data it is (e.g., a photo, video, scanned, free-drawn, audio, appointment). Additionally, data can be tagged with other types (lab order, lab results, referral, hospital related, x-ray, insurance information, scanned in paper, chart, faxed in chart, history, and/or user defined tags). In some embodiments, the system can also put icons on the screen for at least some of the entries in the patient history (e.g., patient history icons 1040). For example, x-rays can have an x-ray icon associated with them. In the example of FIG. 10, the appointment is shown with an appointment icon. Metatags such as "urgent" can also be included to help doctors find specific kinds of entries in a patient's history.

One of the important elements of the form creation is the ability for the system 120 to tie directly into medical billing codes. This allows doctors to automatically generate billing information from their medical records. For example, where a certain number of questions have been answered in a form, the system 120 can generate a bill for a particular level of service. The system 120 can then track whether additional questions are answered during an appointment and increase the billing level. The system 120 can do this by examining billing rules associated with fields 280 and/or forms 270 and creating bills when the billing rules are met. In some embodiments, the system can include billing rules for indicating that additional questions should be asked if specific fields are completed or not completed. The doctor can program these rules into their forms.

In some embodiments, a doctor can define a billing profile for a particularly kind of patient encounter (e.g., carpal tunnel syndrome). A doctor will typically follow a workflow associated with an encounter (an encounter can be a portion or all of an appointment) and the billing profile for that encounter can be associated. In some embodiments, when a doctor selects a particular billing profile, the system 120 can fill in all the descriptions of the problems the patient has (e.g., ICD-9), and/or the procedures performed (e.g., CPT or HCPCS or custom codes), into the fields of one or more forms.

As noted previously, where reference is made to system 120 performing some action, in other embodiments, other elements of system 100 can perform the operation. For example, the tablet 134 can prefill the forms when a particular billing profile is selected. This type of choice may reduce the need for communications with the system 120, but may increase the risk of lost data.

Some tablet computers include camera devices and can be used to take a picture of the patient. The picture can be included from other places as well (e.g., Facebook or other social networking site, Picassa or Flickr or another photo site, or a separate camera). The system 120 can then associate that picture with the patient 220 record.

The doctor can use some of the multimedia capabilities of the iPad to take pictures of injuries or areas of concern on the patient's body, record video of patient's movements or of injuries, or record audio of the patient.

In some embodiments the iPad includes software for reviewing x-rays, lab results and other items. The iPad can then be used by the doctor to directly annotate those items and then forward the annotated documents on (e.g., the doctor can draw on documents using the iPad). In some embodiments the doctor can forward the annotations on by e-mailing the results, or faxing them to another office directly from the iPad. In other embodiments, the doctor can provide a reference to the medical record in the system 120.

Some embodiments of the system 120 support a group chat capability where a practitioner can chat with other members of the practice group. For example, the doctor can select the group chat button and insert a note that a new patient has arrived in exam room two and would like a glass of water. This group chat capability can be implemented on the iPad, other touch devices, and the web interface to the system such that users can all interact across all the platforms that access system 120.

Figure 11:
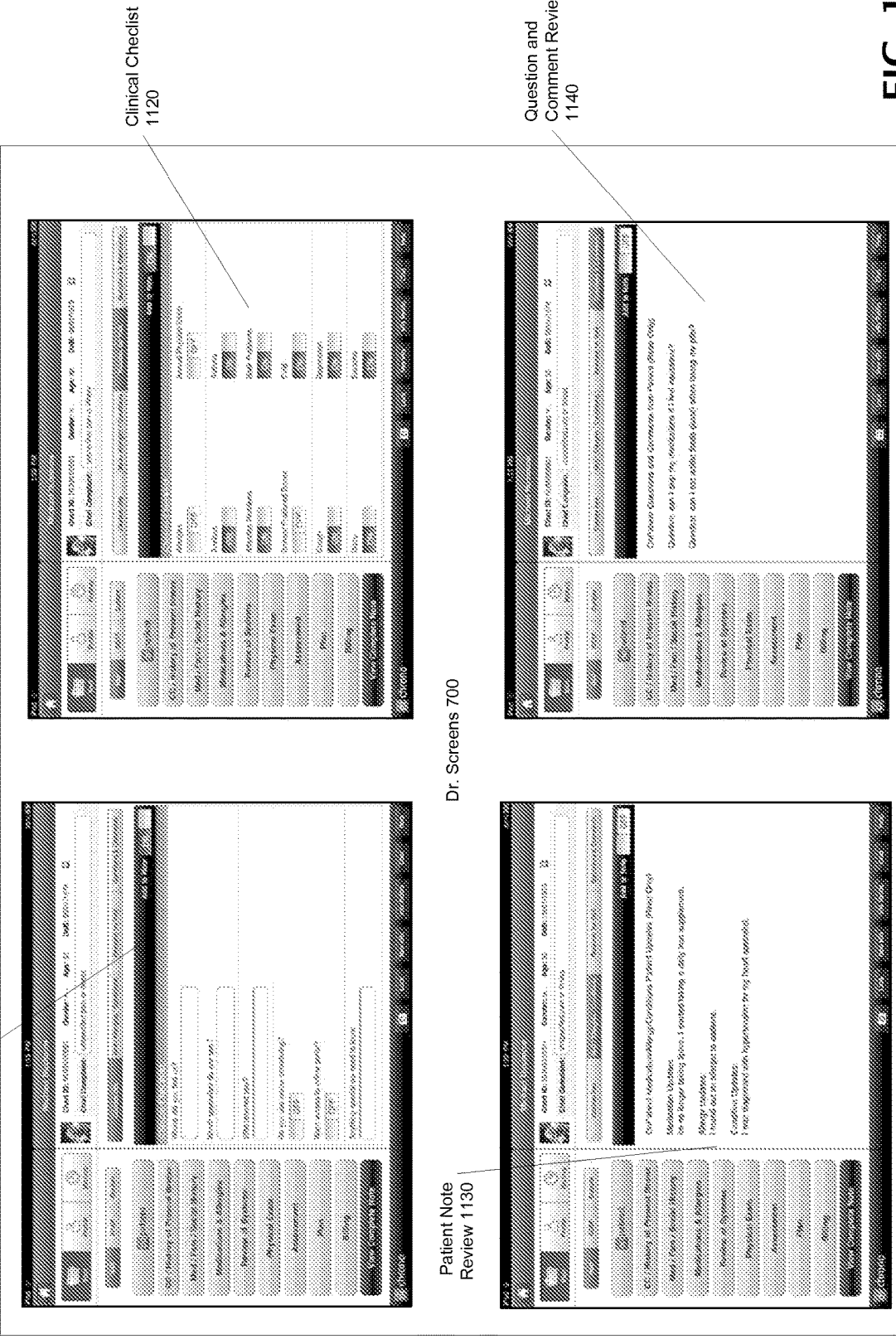
FIG. 11 shows a number of screens allowing the doctor to review the patient onboarding information.

In some embodiments, the doctor can also keep notes about a patient or an appointment by entering data in custom forms, and the notes fields. In some embodiments, the doctor can select whether these notes will become part of the clinical narrative. For example, FIG. 11 illustrates the doctor modifying a custom form that helps capture information about how the patient found the doctor (see patient onboarding Dr. note 1110). The doctor can select to add the note to the clinical narrative or not, by selecting the "add to note" switch. Clinical checklist 1120 illustrates a different kind of form that includes more toggle switches, allowing the doctor to easily interact and enter information with a touch device.

Patient note review 1130 shows how the doctor can review the reasons the patient is coming in for a visit. In this example, a doctor cannot edit the notes the patient entered. Questions and comments 1140 shows how a doctor can review comments and questions from the patient (these comments and questions can be captured during the patient onboarding process).

Note that the relative locations of various elements in the previous displays are example embodiments. In other embodiments, some elements are included on the same screen (e.g., all the forms for a workflow can be displayed in one clinical checklist 630 area), additional information may be included (additional appointment information may be included in the Dr. appointment information 620 area), and/or different elements are located on different displays (e.g. workflow selection, form selection, and the actual forms may not be displayed simultaneously—helpful where the device being used has a smaller screen, such as a mobile phone or smaller tablet computer).

C. Website Examples

The following describes the example website that a doctor can use to help manage his practice. This website allows the doctor to create forms schedule appointments review patient records and manage billing.

Figure 12:
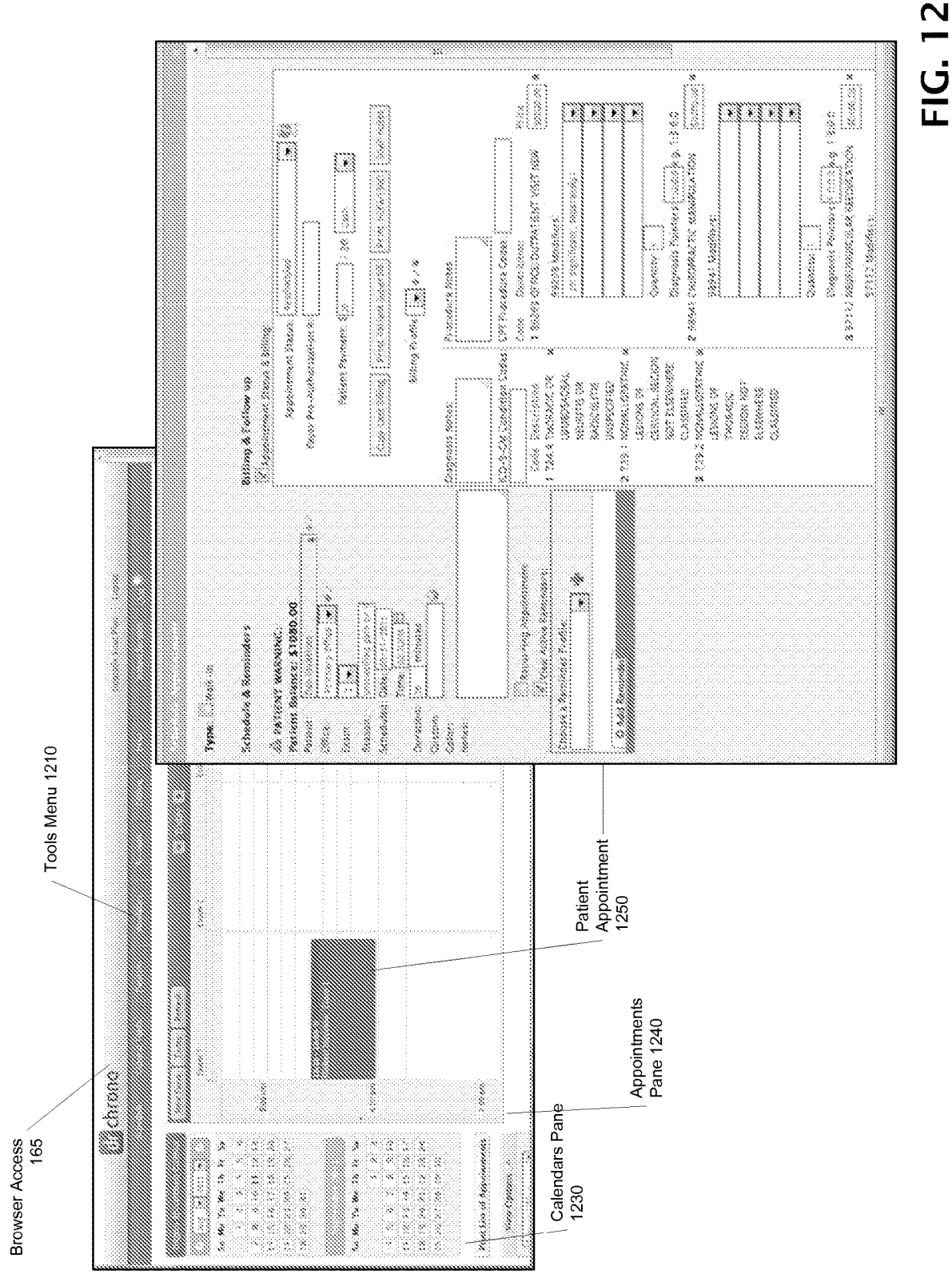
FIG. 12 shows the browser access screens for managing appointments and patient information.

In some systems, the EHR system 120 provides a login screen for a doctor (or login screens for members of a practice group). The doctor can access the login screen via a web browser (browser access 165) on computer 131. The doctor may then be presented with an appointments calendar or a login home screen. In the example of FIG. 12, the browser access 165 includes a tools menu 1210, a calendars pane 1230, an appointments pane 1240, and an open patient appointment 1250. The tools menu 1210 includes options for scheduling appointments, performing clinical tasks, patient tasks, analytics, account tasks, billing, and/or help. The schedule option allows a practice group to manage its appointments, doctors' schedules, and exam rooms. The clinical tools menu allows the doctors to customize their forms and workflows, see a patient dashboard, see patient reminders, see a list of patients, and allow the doctor to see reporting items (e.g., Meaningful Use Reports and Physician Quality Reporting Initiative (PQRI) reports).

FIG. 12 shows a patient appointment 1250 for today in exam room 1. The patient appointment 1250 can be scheduled (e.g., via a pop up window) as shown. In some embodiments, the appointment can also include billing information showing the billing history for the patient. In other embodiments, the system 120 can provide billing or past visit information. In other embodiments, the kinds of information exposed during the scheduling can be selected based upon the permissions set for the type of account. For example, where a scheduling staff member is accessing the system, they may not have access to the same information as the doctor. In some examples, the access can be set as part of rules associated with a given field, form, and/or workflow.

Figure 13:
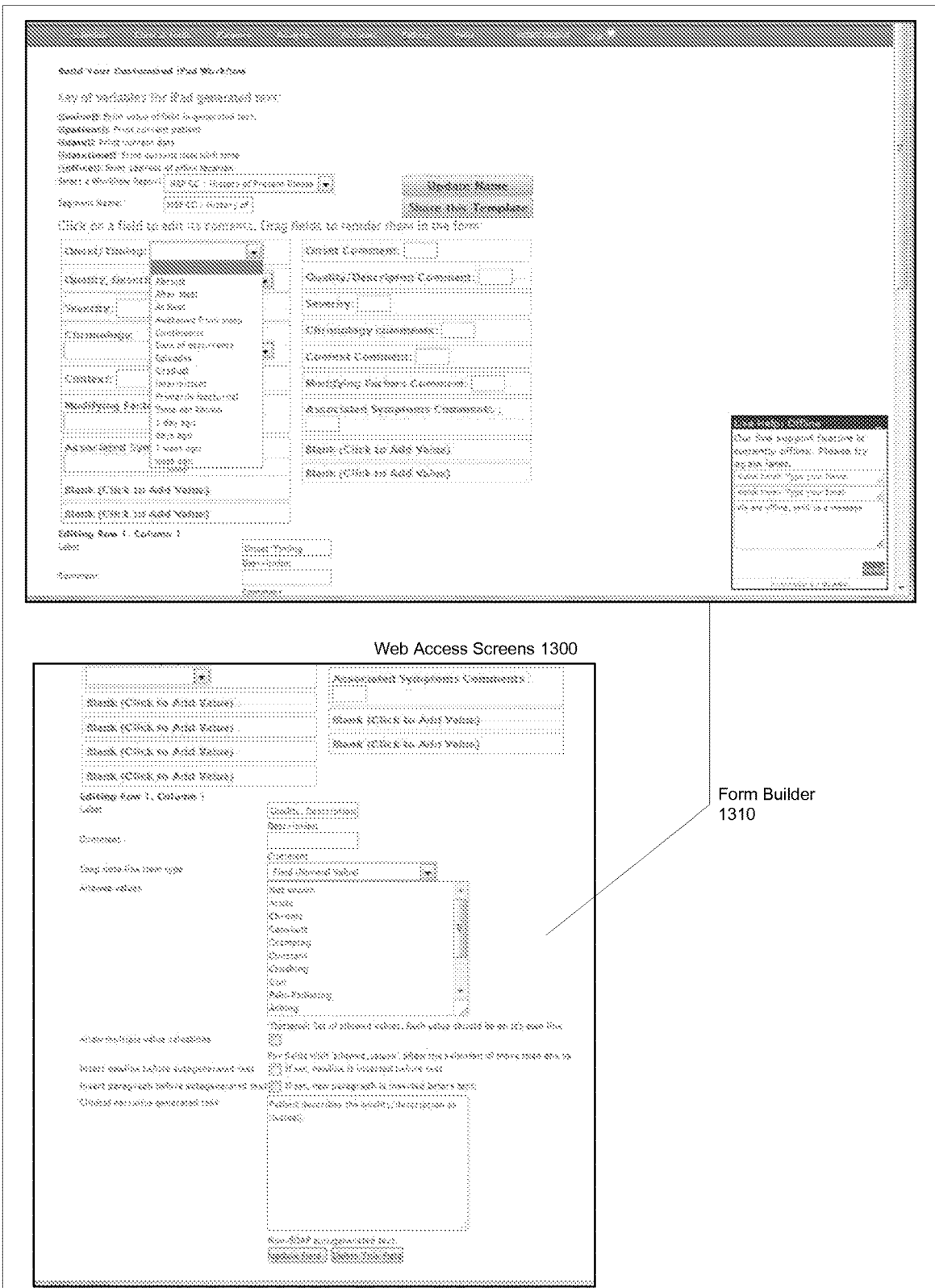
FIG. 13 shows examples of the form builder capability of the system.

FIG. 13 shows that the doctor has selected the clinical tools menu item from the tools menu 1210 for editing their forms and creating new workflows. In this case the doctor has selected the H&P/SOAP workflow editor. In some example systems, the EHR system 120 includes templates for helping doctors customize forms in a set of common workflows (e.g., H&P/SOAP). The form builder 1310 presents a preset template form for the H&P CC/History of the Patient workflow, with the sub-segment of the workflow labeled "H&P CC/History of the Patient." For each field shown, (e.g., Onset/Timing), the doctor can define the kind of data for that field. Example types include toggle, blood pressure, text, numbers, preset list, and others. In some embodiments, the doctor can write scripts or pseudo-scripts to embed data from the storage 122 (e.g., the value of the patient name). In some embodiments of the web access screens 1300, the blue fields can be rearranged by the doctor and edited. For example, the doctor can select and drag and drop the onset/timing field to the second column. The field now appears in the second column and will therefore be updated automatically to appear in the second column on the tablet 134 when this form is accessed.

Each of the fields is user definable and can include predefined values. These values and the fields are editable at the bottom portion of the screen. In this example two columns of fields are showing, to help the doctor visualize where the fields will be presented on the iPad.

The form builder 1310 allows the doctor to further customize the text of the clinical narrative 265. The doctor, can select, for example, whether a new line or paragraph should be created before the text for a specific field. In some embodiments, the form builder 1310 populates a text box with example text for a particular field. In other embodiments, the doctor can see example text for an entire form or workflow (effectively, seeing a corresponding sample clinical narrative).

Also note in this example that live help is available through the system 100 so that the doctor can get help creating a form. In some embodiments, the live help is provided by giving help personnel access to the same storage 122 as the doctor, so that the both the doctor and the help personnel can be viewing the same data structure and/or web screen.

Importantly, in some examples, the system 120 automatically updates the forms stored on the tablet 134 with any changes made in the form builder 1310. In some embodiments, the tablet 134 pulls the latest form information down from the system when the form is activated.

Figure 14:
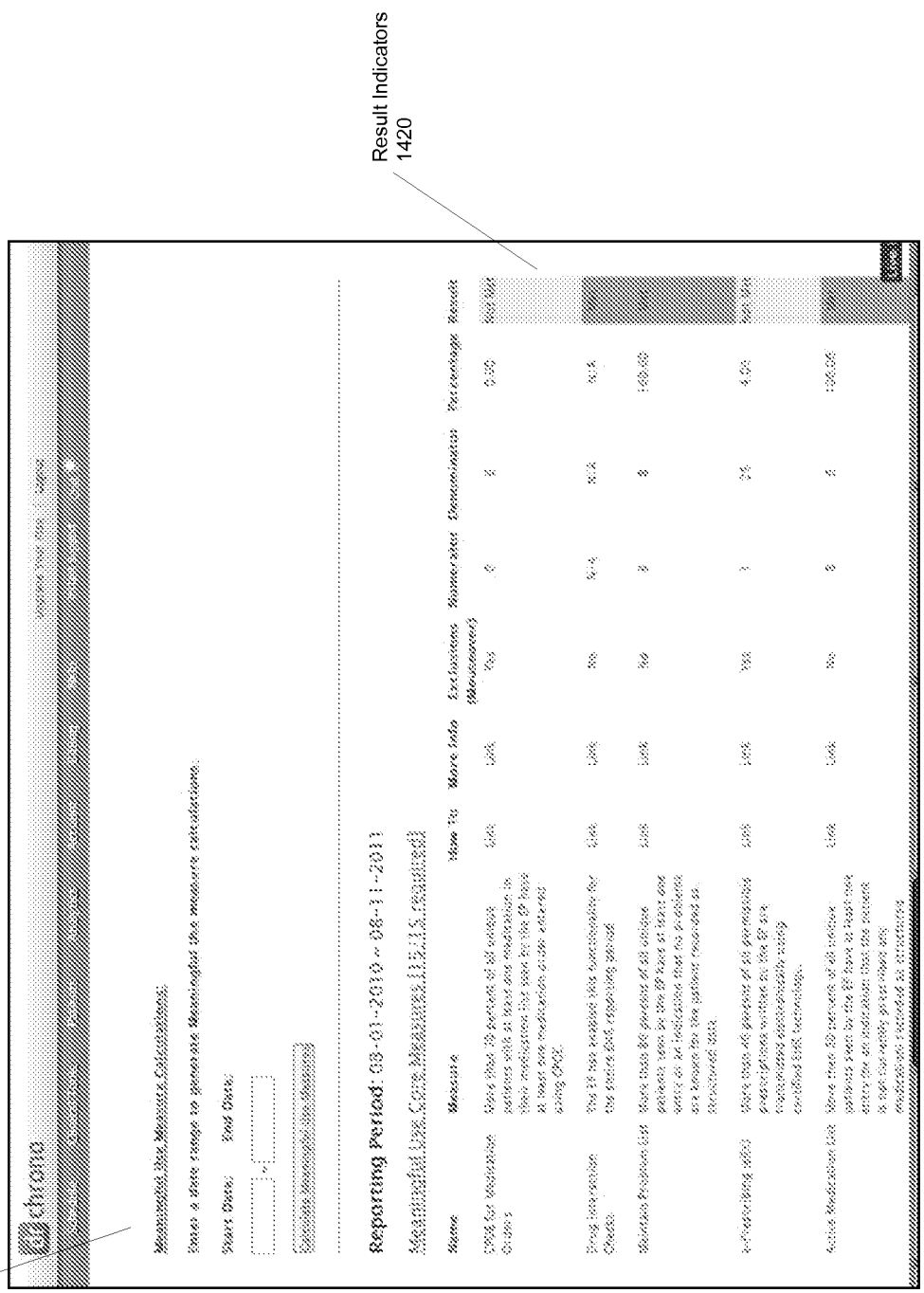
FIG. 14 shows a meaningful measures report.

FIG. 14 shows that the doctor has selected the meaningful measures report from the clinical tools option in the tools menu 1210. Here the doctor can perform a search for measures of their use of the electronic records. The government provides incentives to doctors to use electronic record systems. The meaningful measures report 1410 shows the results of the search including measures of use of electronic records. See FIG. 20 through FIG. 22 for a complete report. However, and helpfully, the system 120 provides an easily readable results column showing whether a particular requirement is met or not met and then color codes those results (result indicators 1420). In other embodiments, checkmarks and X's are used. In other embodiments, other icons are used to indicate how close to compliance with a government requirement the practice group is (e.g., color traffic lights, clouds/sunny, shaded pie charts). In other embodiments, different sections of the report are rolled up into a single score to indicate how well that section's requirements are being met (in some example systems, similar icons are used).

Figure 15:
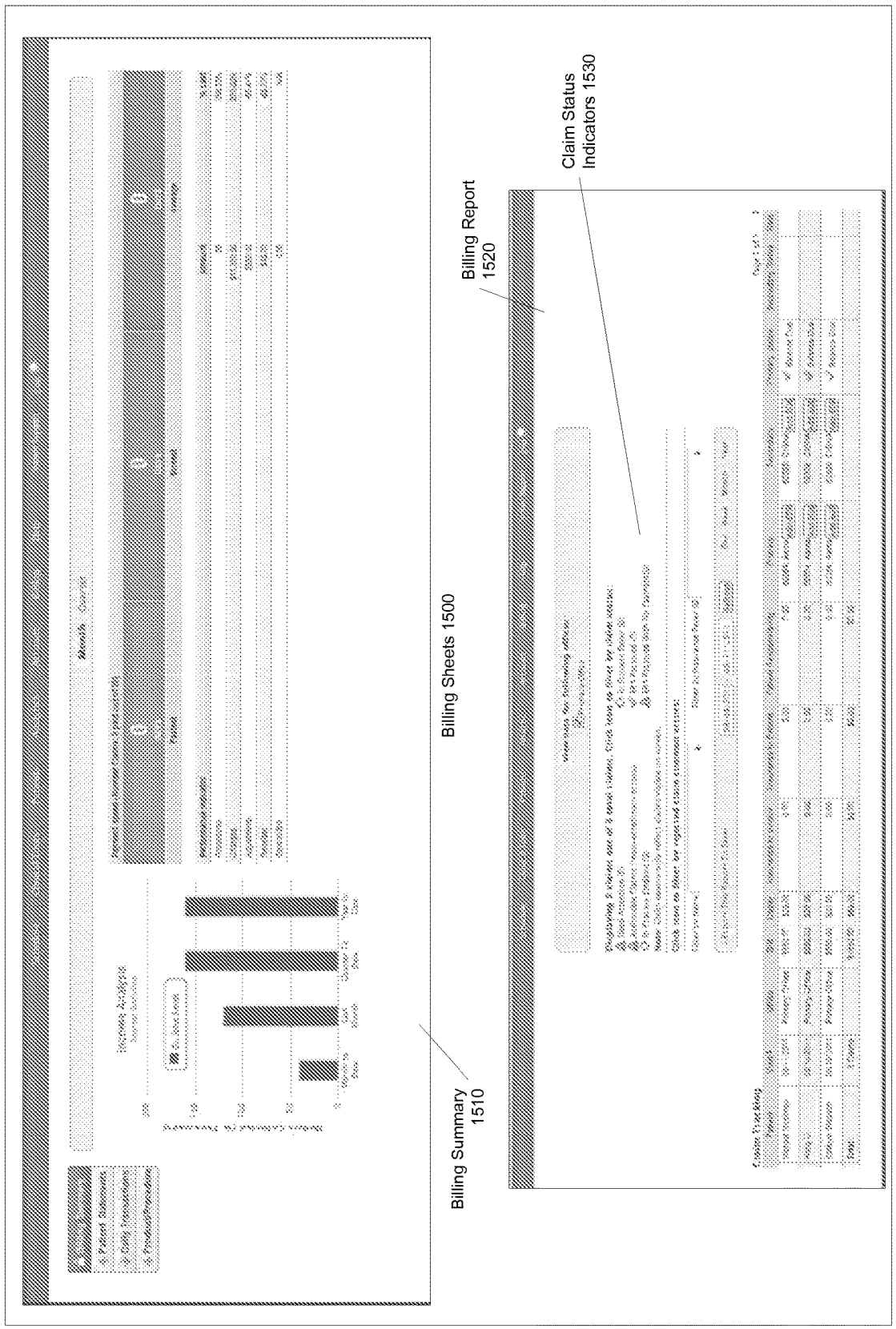
FIG. 15 shows example billing sheets including billing summaries and billing reports.
Figure 16:
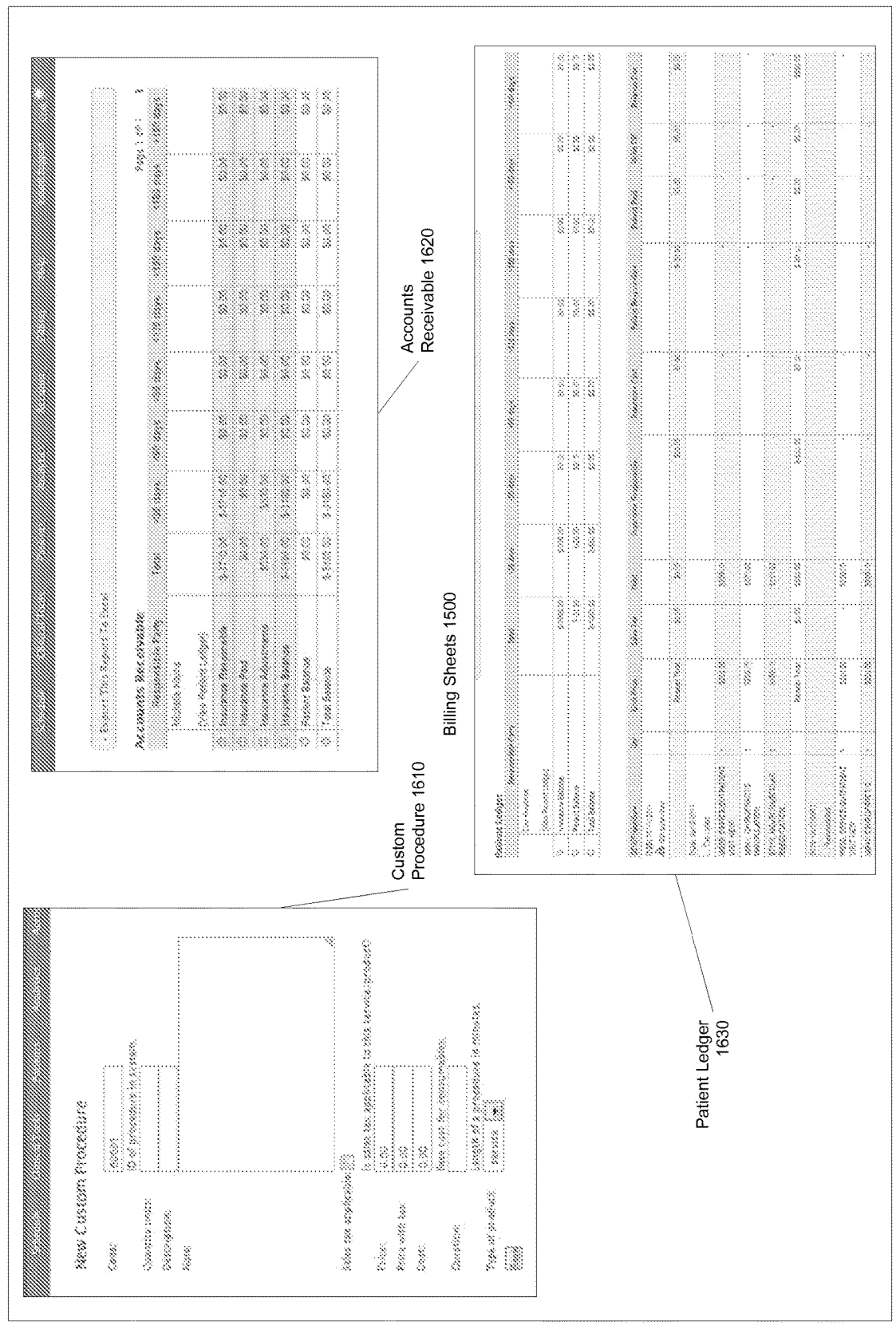
FIG. 16 shows creating new custom codes and includes screens for viewing accounts receivable.

FIG. 15 and FIG. 16 show examples of billing sheets 1500 produced by the system 120. Billing summary 1510 shows an example billing report for a practice group for Dr. John Smith. The report shows a summary of amounts owed, billing aging, adjustments, days to bill, and allows the doctor to accessing per patient, per day and/or product/procedure billing. Other embodiment may include similar types of reports. In some embodiments, the form fields tie to billing codes (e.g., through billing rules, or direct association). These billing codes can then be accessed to provide the doctor with the summary information about the particular patient, procedure, and/or bill. The billing report 1520 can show the status of various bills. The claim status indicators 1530 provide indications of the status of a particular claim in the billing report 1520.

The custom procedure 1610 allows a doctor to enter a billing code for a new custom procedure. The custom procedure can include a code (identifying the code in the system 120), a quantity, a description, note, an indication of whether sales tax is applicable, a price, a price with tax, a cost, an estimate of the amount of time the procedure will take, and/or a type of procedure indicator.

Accounts receivable 1620 shows that the doctor has selected Accounts Receivable menu option. The accounts receivable 1620 shows a report of the accounts receivable for the practice group and allow the doctor to select and drill down on the accounts receivable.

The patient ledger 1630 shows that the doctor selected the patient ledger and allows for a detailed view of the types of procedures that a particular patient has had and the payments by that patient.

Figure 17:
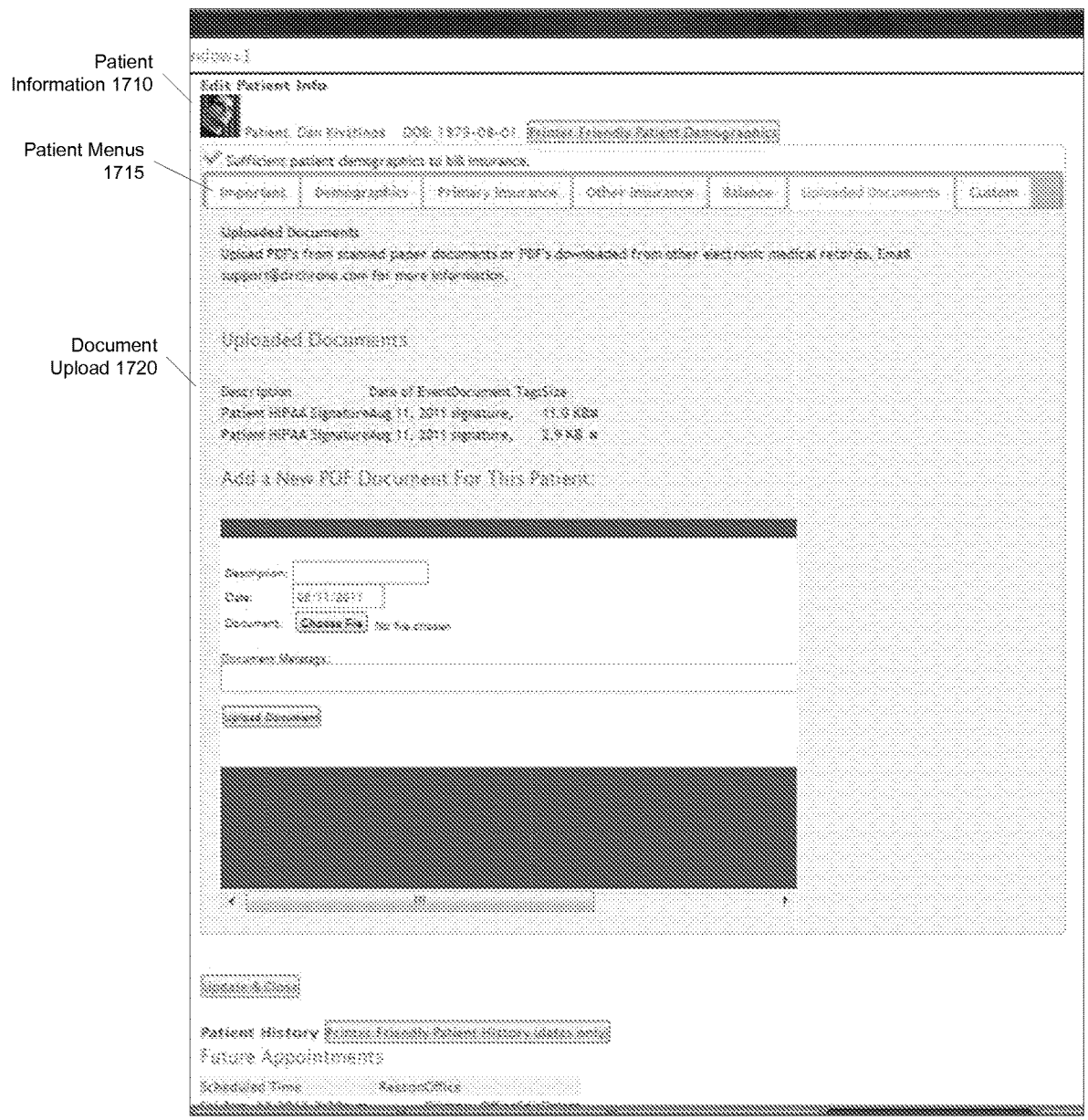
FIG. 17 shows sample patient information and document upload capabilities.

FIG. 17 illustrates some of the patient information 1710 that is available through the system 120 via the browser access 165. The patient menus 1715 allow the doctor to access important information about the patient, demographics, primary insurance, other insurance, balance due, upload documents, or access a custom form for adding information to the patient information. The information on the screen is similar to that provided to the iPad. In this example, the doctor can upload additional documents to the patient information (e.g., PDFs). The doctor has selected the upload patient menus 1715 option and can use the document upload 1720 to upload documents to the patient's record.

D. Additional Form Creation

Figure 18:
FIG. 18 shows an additional interface for designing forms.

FIG. 18 shows another type of interface for building forms for a tablet computer (in this example, an iPad). The form builder 1810 importantly shows a sample display of the iPad so that user can see how a form will look when finalized.

Note, in some embodiments, the form on the tablet computer 134 takes only a portion of the entire display when the tablet is oriented horizontally, and takes up almost the entire display when the tablet is oriented vertically. This helps the doctor fit more of a form on the screen when completing forms. In the example of FIG. 18, it is assumed the doctor will be using the form primarily in the vertical position. In other embodiments, the user can select to see the space for form creation in either of the vertical position or the horizontal position (an example of the space available for a form in such a position is show by the visible portion of the clinical checklist 630 in FIG. 6.

The form builder 1810 can be accessed via the web browser based custom form designer 161. The form builder 1810 can include a form tools 1810 menu, a form identification section 1830, a form field types 1840, a form canvas

1850, and example form fields 1860. The form tools 1820 allow the user to select an existing form, create a new form, and organize forms. The form canvas 1850 shows example form fields 1860 selected for a new form.

Importantly, a user can select a field type from the form field type 1840, and drag and drop the field type onto the form canvas 1850 to create a new form field 1860. The system 120 then fits the field into the location on the form canvas 1850. The picture of the iPad helps the user see how the form will look on the particular device. In other embodiments, the user can select other device images to display and see how a form will look on that device. In some embodiments, the user can select different form layouts for different devices. The types of fields include short text field, long text field, switch field, multiple select field, single select field, fraction fields, and paragraph field. The user is allowed to drag and drop any of these fields from the left of the screen onto the picture of the iPad. The user can rearrange the order of these fields or edit them and their labels.

Figure 19:
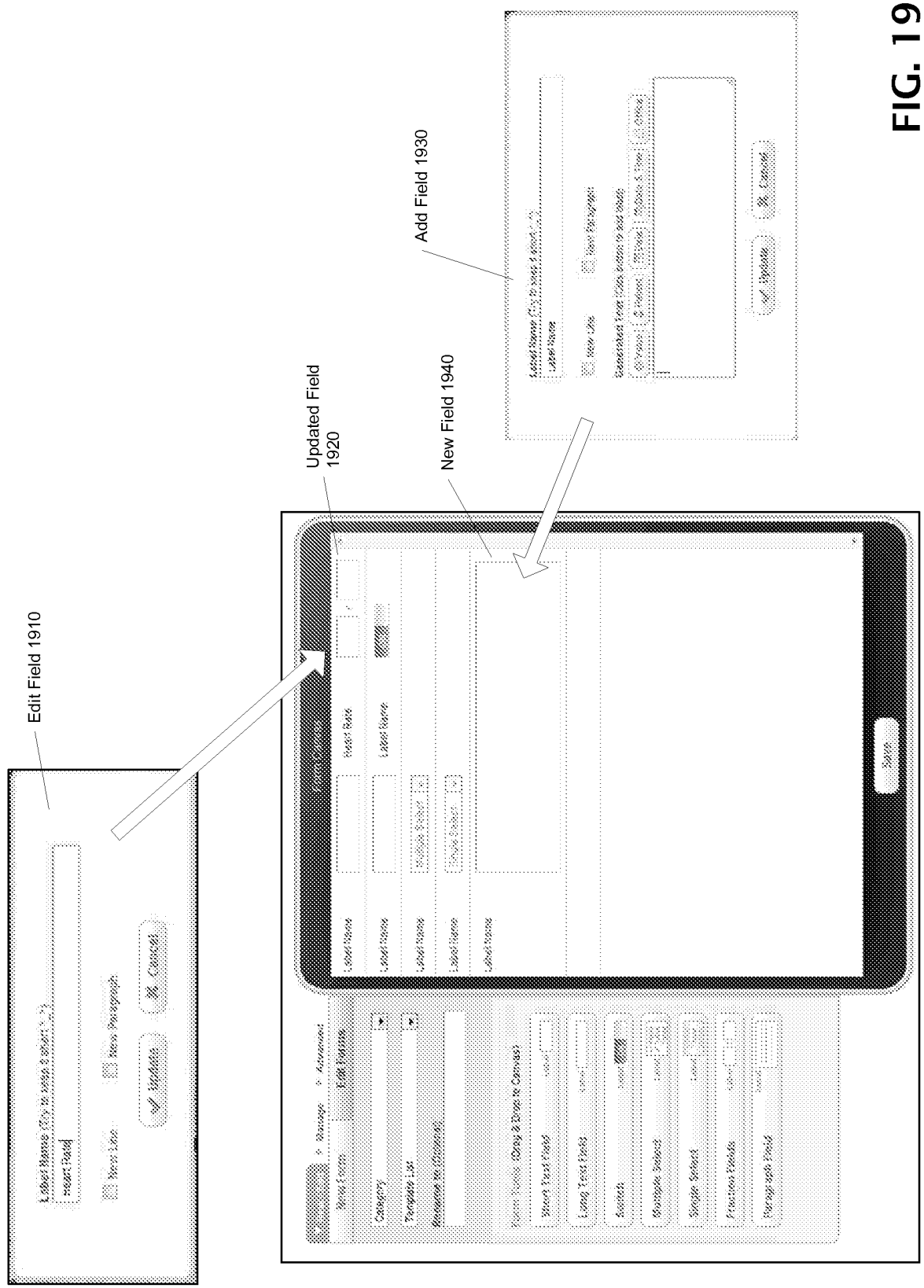
FIG. 19 shows an example form being modified.

FIG. 19 shows modifying and adding fields to the form fields 1860. When the user selects the updated field 1920, a popup appears (edit field 1910) allowing the user to edit the label for the field. The updated field shows that the heart rate field name has been properly changed on the form. In some example systems, the display is grayed out while the popup is present. The user has also selected to add a new field 1940 by selecting the corresponding field type. The add field 1930 window appears allowing the user to customize the field. The new field 1940 is a text field that can include predefined variables or information about those variables. For example the value of a field can be automatically inserted into the text for that field. Additionally, the patient name, the date, date and time, and/or the office, can all be automatically generated for a field. This is particularly helpful in creating notes for the doctor.

E. Example Templates

The following shows example custom form templates. The first template is for "History and Physical Clinical Chart—History of Present Illness" (Table 1) and a second template is for "Additional Information" form for patient onboarding (Table 2).

Each of the tables include doctor 120 identifying information, report name (for the associated workflow), and field definitions. The field definitions can include the name of the field, the type of the field, and billing profile information, among other things.

TABLE 1

| History and Physical Clinical Chart - History of Present Illness |
|---|
| Doctor: Dr. John Smith<br>Report Name: H&P CC / History of Present Illness<br>Fields:<br>Field[0]: Label='Onset/Timing', comment='', field_type='String', row='0', column='0',<br>    subjective_generated_text='History of Present illness:<br>Patient explains the timing/onset for illness to be {{value}}.', objective_generated_text='', assessment_generated_text='', plan_generated_text='', clinical_narrative_generated_text='Patient explains the timing/onset for illness to be {{value}}.<br>    ', billing_profile='None',<br>Field[1]: Label='Context', comment='', field_type='String', row='4', column='0',<br>    subjective_generated_text='The context in which the patient's illness occurred includes: {{value}}.<br>    ', objective_generated_text='', assessment_generated_text='', plan_generated_text='', clinical_narrative_generated_text='The context in which the patient's illness occurred includes: {{value}}.<br>    ', billing_profile='None',<br>Field[2]: Label='Modifying Factors', comment='', field_type='String', row='5', column='0',<br>    subjective_generated_text='', objective_generated_text='', assessment_generated_text='', plan_generated_text='', clinical_narrative_generated_text='', billing_profile='None',<br>Field[3]: Label='Quality, Description ', comment='', field_type='String', row='1', column='0',<br>    subjective_generated_text='Patient describes the quality/description as {{value}}. ',objective_generated_text='', assessment_generated_text='', plan_generated_text='', clinical_narrative_generated_text='Patient describes the quality/description as {{value}}.<br>    ', billing_profile='None',<br>Field[4]: Label='Severity', comment='', field_type='String', row='2', column='0',<br>    subjective_generated_text='Patient describes severity as {{value}}.', objective_generated_text='', assessment_generated_text='', plan_generated_text='', clinical_narrative_generated_text='Patient describes severity as {{value}}.<br>    ', billing_profile='None',<br>Field[5]: Label='Onset Comment', comment='', field_type='String', row='0', column='1',<br>    subjective_generated_text='{{value}}', objective_generated_text='', assessment_generated_text='', plan_generated_text='', clinical_narrative_generated_text='{{value}}<br>    ', billing_profile='None',<br>Field[6]: Label='Context Comment', comment='', field_type='String', row='4', column='1',<br>    subjective_generated_text='{{value}}', objective_generated_text='', assessment_generated_text='', plan_generated_text='', |

TABLE 1-continued

History and Physical Clinical Chart - History of Present Illness clinical_narrative_generated_text='{{value}}
', billing_profile='None',
Field[7]: Label='Modifying Factors Comment', comment='',
field_type='String', row='5', column='1',
subjective_generated_text='{{value}}', objective_generated_text='',
assessment_generated_text='', plan_generated_text='',
clinical_narrative_generated_text='{{value}}
', billing_profile='None',
Field[8]: Label='Quality/Descripton Comment', comment='',
field_type='String', row='1', column='1',
subjective_generated_text='{{value}}', objective_generated_text='',
assessment_generated_text='', plan_generated_text='',
clinical_narrative_generated_text='{{value}}
', billing_profile='None',
Field[9]: Label='Severity', comment='', field_type='String', row='2',
column='1',
subjective_generated_text='{{value}}', objective_generated_text='',
assessment_generated_text='', plan_generated_text='',
clinical_narrative_generated_text='{{value}}
', billing_profile='None',
Field [10]: Label='Chronology', comment='', field_type='String',
row='3', column='0',
subjective_generated_text='', objective_generated_text='',
assessment_generated_text='', plan_generated_text='', clinical_narrative_generated_text='',
billing_profile='None',
Field[11]: Label='Chronology comments', comment='',
field_type='String', row='3', column='1',
subjective_generated_text='{{value}} ',objective_generated_text='',
assessment_generated_text='', plan_generated_text='',
clinical_narrative_generated_text='{{value}}
', billing_profile='None',
Field[12]: Label='Associated Symptoms ', comment='',
field_type='String', row='6', column='0',
subjective_generated_text='Associated symptoms: {{value}} ',
objective_generated_text='', assessment_generated_text='', plan_generated_text='',
clinical_narrative_generated_text='Associated symptoms: {{value}}
', billing_profile='None',
Field [13]: Label='Associated Symptoms Comments ',comment='',
field_type='String', row='6', column='1',
subjective_generated_text='{{value}}', objective_generated_text='',
assessment_generated_text='', plan_generated_text='',
clinical_narrative_generated_text='{{value}}
', billing_profile='None', Second Table - Additional Information Example: Patient Onboarding - Additional Information
Doctor: Dr. John Smith
Report Name: OnPatient Additional Info
Fields:
Field[0]: Label='Where did you find us?', comment='',
field_type='String', row='0', column='0',
subjective_generated_text='', objective_generated_text='',
assessment_generated_text='', plan_generated_text='',
clinical_narrative_generated_text='Where the patient found our practice: {{value}}',
billing_profile='None',
Field[1]: Label='Which specialists do you see?', comment='',
field_type='String', row='1', column='0',
subjective_generated_text='', objective_generated_text='',
assessment_generated_text='', plan_generated_text='',
clinical_narrative_generated_text='Specialists patient is currently seeing:',
billing_profile='None',
Field[2]: Label='Who referred you? ', comment='', field_type='String',
row='2', column='0',
subjective_generated_text='', objective_generated_text='',
assessment_generated_text='', plan_generated_text='',
clinical_narrative_generated_text='Patient was referred by: {{value}} ',
billing_profile='None',

| Second Table - Additional Information |
| --- |
| Field[3]: Label='Anything special we need to know', comment='',<br>field_type='String', row='5', column='0',<br>    subjective_generated_text='', objective_generated_text='',<br>assessment_generated_text='', plan_generated_text='',<br>clinical_narrative_generated_text='Additional comments made by patient: {{value}}.',<br>billing_profile='None',<br>    Field[4]: Label='Do you use online scheduling?', comment='',<br>field_type='Checkbox', row='3', column='0',<br>    subjective_generated_text='', objective_generated_text='',<br>assessment_generated_text='', plan_generated_text='',<br>clinical_narrative_generated_text='Patient uses online scheduling: {{value}}',<br>billing_profile='None',<br>    Field[5]: Label='Want access to online portal?', comment='',<br>field_type='Checkbox', row='4', column='0',<br>    subjective_generated_text='', objective_generated_text='',<br>assessment_generated_text='', plan_generated_text='',<br>clinical_narrative_generated_text='Patient would like access to online patient portal.',<br>billing_profile='None', |

F. Meaningful Use Report

Figure 20:
FIG. 20 shows an extended meaningful use report.
Figure 21:
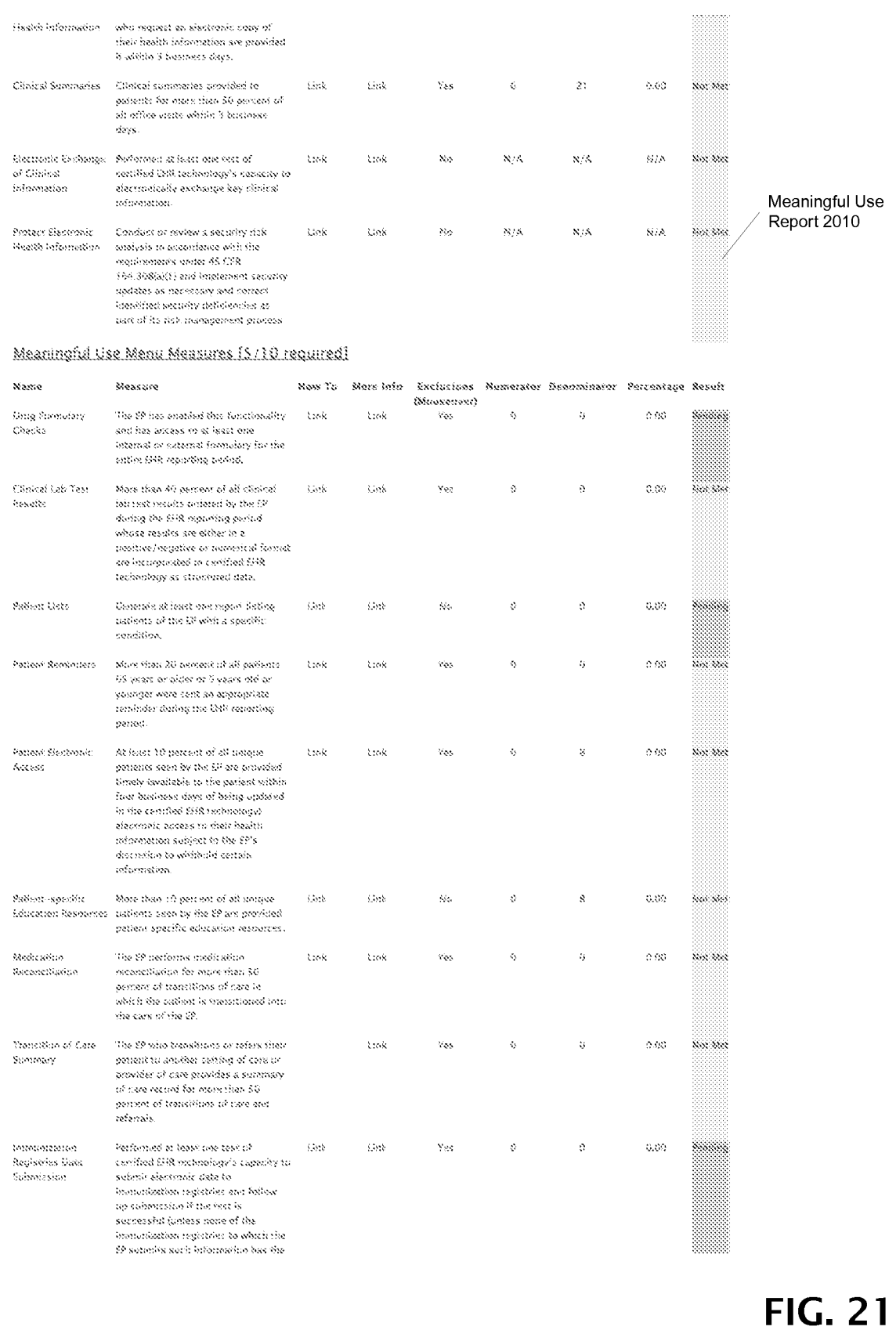
Figure 22:
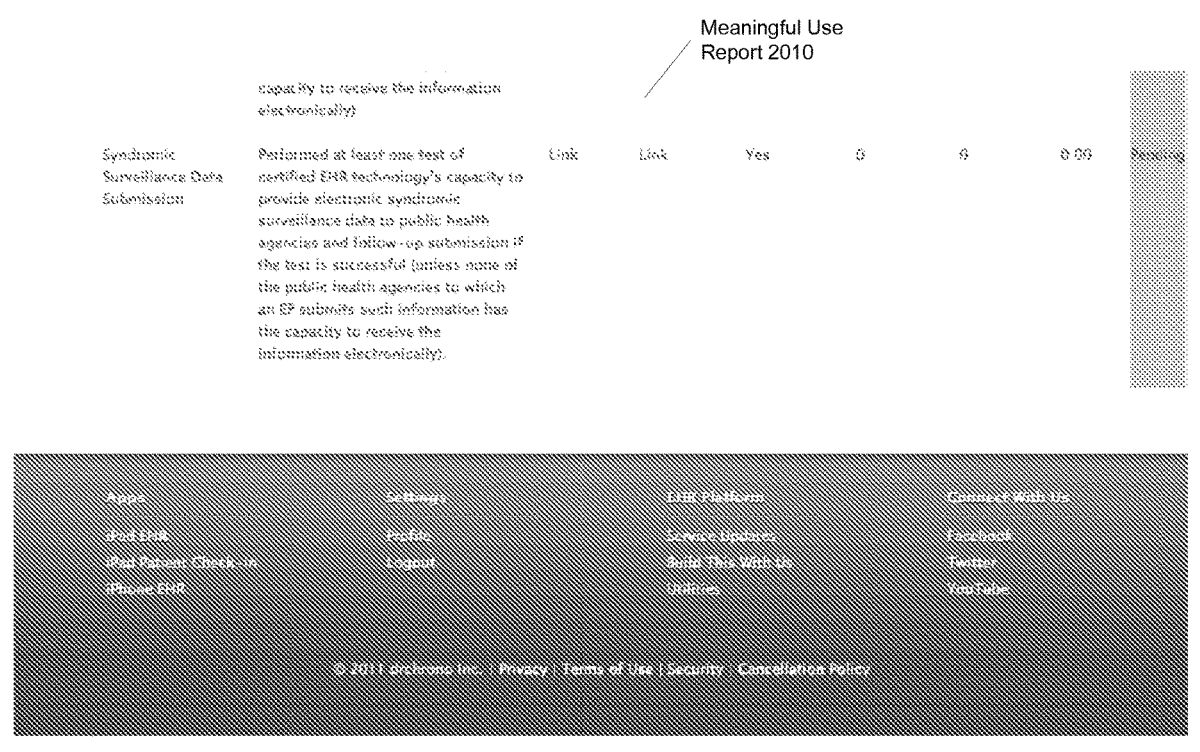

FIG. 20, FIG. 21, and FIG. 22 show a sample meaningful use report 2010 for a selected time period. Presently in the United States, doctors are expected to demonstrate meaningful use of an EHR on at least 15 criteria by 2014. This report provides an easy way to document compliance for the doctor as well as to troubleshoot any problem areas. In this example, the report provides easy reference to the criteria, the measurement methodology, links to additional information, standard exclusions, and the values for the time period. Finally, the percentage compliance is documented numerically and narratively, e.g. met vs. not met. The compliance documentation can be supplemented with additional visual indications, colors in this report (green=met, yellow=not met, grey=pending). Other visual indicators such as smiley faces, weather icons, and further color signals could be used. Additionally, some embodiments may present an overall summary at the top, bottom, or elsewhere, of the report summarizing whether e.g., 15-of-15 criteria are met.

G. Conclusion and Additional Embodiments

We have now described a system and processes that provides an EHR offering with cloud-based, or SaaS, storage and infrastructure as well as easy use of mobile and tablet devices by doctors, staff and patients to provide an improved medical practice.

Additional embodiments allow doctors to post their medical forms on the EHR system (or references to the forms), allowing others to comment on the forms, and/or vote on the quality/utility of the forms. Doctors can then select forms to use in their practice group and/or modify those forms.

In some embodiments, the rating is generated from recommendations, references on social networking recommendations, and/or twitter trends.

In some embodiments, the EHR system 120 allows the users to search for forms based upon metadata tagging the forms (e.g., the workflow name, the kind of practice the form applies to).

In some embodiments, a form field value can be conditional—e.g., if value 290 is x of y answers are completed, then cause an event (e.g., billing). This allows users to create forms that can notify the user that if a certain set of additional questions are answered, then a billing code will be achieved. In some embodiments, the field can be defined to show how many of the answers have been completed for a billing code and how many more are needed to reach the next billing code.

In some embodiments, some fields are of type tri-state, e.g., yes/no/blank, not just yes/no. This can force the user to indicate that the field is supposed to be blank.

Some embodiments support real time collaboration in a medical group and allow for simultaneous access to a patient's EHR. In some embodiments, only changed fields are sent to the system 120 versus all the values of fields in the form. To handle conflicts, when two people access the same field, different embodiments use different processes (e.g., last one wins; first to lock the record wins and a warning may be sent to the other user; duplicate the entry with both modifications and flag the conflict; allow select people to overwrite others (e.g., doctors can overwrite some fields); heavily filled out fields overwrite; and if more than 50% of the form has been changed, then overwrite the form).

In some embodiments, the system 120 notifies staff if the system 120 loses contact with the tablet computer 134. This is helpful in ensuring that the tablet computers 134 do not get lost or stolen.

In some embodiments, the application 171 allows the doctor to annotate PDF documents and images. This can be done by embedding the PDF or image as a background in a form, providing drawing tools for the application 171, and capturing annotations using those drawing tools. Some embodiments include free form drawing fields, allowing direct drawing on images within a form. In some embodiments, the doctor view an image in a forms drawing field and can use a finger or a stylus on the tablet computer 134 to draw directly on the image (e.g., circle an area of concern on a picture of an x-ray).

In some embodiments, the clinical narrative and/or other portions of a patient's electronic health record can be shared. Examples include emailing, generating a fax, generating a physical letter and mailing it. In some embodiments, the narrative can include a link, address, or graphic (e.g., unique bar code) that uniquely identifies the narrative. Other doctors and practitioners could then access the narrative using the unique identifier. In some embodiments, the unique identifier is associated with a HIPAA compliance notice. Portions of the narrative and/or all of a patient's EHR can be viewed or downloaded from the system 120 by a patient.

In some embodiments, the application 171 can be used to schedule lab appointments and procedures (via lab ordering system 114).

Other embodiments support other types of practices and professionals, for example, dentists, optometrists, pharmacists, and/or veterinarians.

In some embodiments, where a doctor sends a fax of a clinical narrative to another doctor, and the receiving doctor is also a subscriber to the EHR, the second doctor may receive an email rather than the fax. The email would then identify the narrative.

Some embodiments include additional services and software to support credit/debit card transactions with the tablet device. For example, some embodiments use the Square system to allow patients to pay directly. The system 120 records that the payment has been received. In some embodiments, the Square software works with the patient application. In other applications, the Square payment information is sent to the system 120 and is associated with the patient's accounting records.

In some embodiments, the system 120 supports referral tracking. This allows doctors to determine where a patient has been referred from, and/or whether patients are going to doctors to whom they have been referred. The system 120 includes a doctor identifier with a patient's record (and/or a particular appointment). Referrals can be tagged where, for example, a doctor refers a patient to another doctor and the other doctor accesses that patient's medical record. In other cases, the referring doctor's identifier is associated with a patient's appointment (e.g., when the staff create the appointment). The identifier can be a National Provider Identifier (NPI), a unique doctor identifier created by the system 120, or some other ID that uniquely identifies a doctor (in some embodiments, a doctor may have more than one identifier). The referral tracking may be important where an HMO requires tracking and/or compliance with referral rules.

In some embodiments, forms 270 can include information about the location of fields 280 in that form. In other embodiments, the fields 280 keep information about their location in a form 270. In other embodiments, location information is kept in another table outside of the forms 270 and the fields 280. In some embodiments, the order of forms in a workflow can be defined by a user. In some embodiments, the order that text is created from forms in a workflow can be separately defined by a user.

Any data structures and code described or referenced above are stored according to many embodiments on a computer-readable storage medium, which may be any device or medium that can store code and/or data for use by a computer system. This includes, but is not limited to, volatile memory, non-volatile memory, application-specific integrated circuits (ASICs), field-programmable gate arrays (FPGAs), magnetic and optical storage devices such as disk drives, magnetic tape, CDs (compact discs), DVDs (digital versatile discs or digital video discs), or other media capable of storing computer-readable media now known or later developed.

The preceding description is presented to enable the making and use of the invention. Various modifications to the disclosed embodiments will be apparent, and the general principles defined herein may be applied to other embodiments and applications without departing from the spirit and scope of the invention. Thus, the invention is not intended to be limited to the embodiments shown, but is to be accorded the widest scope consistent with the principles and features disclosed herein. The scope of the invention is defined by the appended claims.

What is claimed is:

1. A system for managing and storing electronic medical records, the system comprising:
    a first computer having a medical form, the medical form including a set of fields;
    a tablet computer having an application, the application for accessing and displaying the medical form, the application further for receiving form field values and for transmitting the form field values to the first computer after entry by a first patient, the application configured for:
    receiving a first signal on the tablet computer, the first signal identifying the first patient;
    receiving a second signal indicating that input will be received from the first patient and further requiring that the tablet computer is to lock out access to other patient information regarding patients other than the first patient, the second signal transforming the tablet computer into a restricted access tablet computer that filters information for display to the first patient in a patient role;
    at a first time, displaying a first indication that the tablet computer was successfully transformed into a restricted access tablet computer and identifying the first patient, and displaying a control to advance to displaying a medical form;
    at a second time, presenting a first page of the medical form on the restricted access tablet computer including a first set of fields, wherein the first set of fields includes a first subset of fields to be completed by the first patient, the first subset of fields comprising information about the patient, permitting editing in some of the first set of fields and displaying a first control to advance to a next page of the medical form;
    at a third time, presenting a second page of the medical form on the restricted access tablet computer including a second set of fields, wherein the second set of fields includes a second subset of fields to be completed by the first patient and one or more prepopulated fields, permitting the addition of comments to fields but not allowing the editing of the fields, wherein the addition of a comment to the fields triggers a third signal requesting review by a practitioner and displaying a second control to advance to a next page of the medical form;
    at a fourth time, presenting a third page of the medical form on the restricted access tablet computer and displaying a third control to advance to locking the medical form;
    receiving a fourth signal on the restricted access tablet computer indicating the first patient has entered information responsive to at least some of the fields of the form and indicating selection of the third control to advance to locking the medical form;
    locking and hiding the medical form and displaying a second indication that the tablet computer was successfully locked so that it cannot be unlocked by the first patient or other patients in the patient role.

2. The system of claim 1 wherein the application supports access to multiple different accounts within a medical practice group, wherein at least some accounts have restricted access to some of the form fields.

3. The system of claim 2 wherein the application supports a staff account and a doctor account and wherein the staff account does not have access to all the form fields that the doctor account can access.

4. The system of claim 2 further comprising a program to resolve conflicts where two values have been simultaneously edited for the same field.

5. The system of claim 2 wherein a medical form can be associated with a set of billing codes and billing rules and where the system provides an indication when sufficient form fields have been completed to satisfy at least one billing rule.

6. A computer-implemented method for completion of an electronic medical record for a first patient using a tablet computer, the method comprising:
- receiving a first signal on the tablet computer, the first signal identifying the first patient;
- receiving a second signal indicating that input will be received from the first patient;
- the second signal further identifying that the tablet computer is to lock out access to patient information regarding patients other than the first patient, the second signal transforming the tablet computer into a restricted access tablet computer that filters information for display to the first patient in a patient role;
- at a first time, displaying a first indication that the tablet computer was successfully transformed into a restricted access tablet computer and identifying the first patient, and displaying a control to advance to displaying a medical form;
- at a second time, presenting a first page of the medical form on the restricted access tablet computer including a first set of fields, wherein the first set of fields includes a first subset of fields to be completed by the first patient, the first subset of fields comprising information about the patient, permitting editing in some of the first set of fields and displaying a first control to advance to a next page of the medical form;
- at a third time, presenting a second page of the medical form on the restricted access tablet computer including a second set of fields, wherein the second set of fields includes a second subset of fields to be completed by the first patient and one or more prepopulated fields, permitting the addition of comments to fields but not allowing the editing of the fields, wherein the addition of a comment to the fields triggers a third signal requesting review by a practitioner, and displaying a second control to advance to a next page of the medical form;
- at a fourth time, presenting a third page of the medical form on the restricted access tablet computer and displaying a fourth control to advance to locking the medical form;
- receiving a third signal on the restricted access tablet computer indicating the first patient has entered information responsive to at least some of the fields of the form and indicating selection of the control to advance to locking the medical form;
- locking and hiding the medical form and displaying a second indication that the tablet computer was successfully locked so that it cannot be unlocked by the first patient or other patients in the patient role.

7. The method of claim 6 wherein the first indication includes a graphical representation of transferring the restricted access tablet computer to a patient and the second indication includes a graphical representation of transferring the restricted access tablet computer to a medical group staff member.

8. The method of claim 6 wherein the second indication includes an image showing the restricted access tablet being passed to the patient and wherein none of the patient information is shown on the restricted access tablet computer while the second image being displayed.

9. The method of claim 6 wherein the receiving the third signal includes the restricted access tablet computer receiving a digital representation of the patient's signature.

10. The method of claim 9 wherein the receiving the third signal includes receiving a signal indicating at least a portion of a patient sign in process is complete.

* * * * *